US005721096A

United States Patent [19]
Karathanasis et al.

[11] Patent Number: 5,721,096
[45] Date of Patent: Feb. 24, 1998

[54] METHODS OF SCREENING FOR COMPOUNDS WITH ABILITY TO ALTER APOLIPOPROTEIN AI GENE EXPRESSION

[75] Inventors: Sotirios K. Karathanasis, Roslindale; John A.A. Ladias, Boston, both of Mass.; Jeffrey N. Rottman, St. Louis, Mo.; Russell L. Widom, Brookline, Mass.

[73] Assignee: Children's Medical Center Corporation, Boston, Mass.

[21] Appl. No.: 255,471

[22] Filed: Jun. 8, 1994

Related U.S. Application Data

[62] Division of Ser. No. 142,838, Oct. 25, 1993, abandoned, which is a continuation of Ser. No. 784,472, Oct. 24, 1991, abandoned, which is a continuation-in-part of Ser. No. 645,139, Jan. 24, 1991, abandoned.

[51] Int. Cl.$^6$ .............................. C12Q 1/68; G01N 33/53
[52] U.S. Cl. .................................................. 435/6; 435/7.1
[58] Field of Search ............................... 435/6, 7.1, 7.93, 435/172.1; 536/23.1, 23.5, 24.1

[56] References Cited

U.S. PATENT DOCUMENTS 5,580,722  12/1996  Foulkes et al. ............................. 435/6

FOREIGN PATENT DOCUMENTS

WO 91/01379  2/1991  WIPO .

OTHER PUBLICATIONS

Ladias, J.A.A., and Karathanasis, S.K., *J. Cell. Biochem.: Abstracts from the 19th UCLA Symposia of Molecular & Cellular Biology, Jan. 27 –Feb. 8, 1990*, 14B:309.

Ladias, J.A.A., and Karathanasis, S.K., *FASEB J.: Abstracts from the American Society for Biochemistry and Molecular Biology and The American Association of Immunologists Joint Meeting, Jun. 4–7, 1990*: A2096.

Ladias, J.A.A., and Karathanasis, S.K., *Abstracts from the 20th Steenbock Symposium on Molecular Biology of Atherosclerosis, Jun. 3–5, 1990*, Abstract #P–15.

Ladias, J.A.A., and Karathanasis, S.K., *Circulation: Abstracts from the 63rd Scientific Sessions, Nov. 12–15 (1990)* 82(4)III–L (Oct. 1990).

Widom, R.L., et al., "Synergistic Interactions Between Transscription Factors Control Expression of the Apolipoprotein AI Gene In Liver Cells", *Mol. Cell. Biol.* 11:677–687 (Feb. 1991).

Ladias, J.A.A., and Karathanasis, S.K., "Regulation of the Apolipoprotein AI Gene by ARP-1, A Novel Member of the Steroid Receptor Superfamily", *Science* 251:561–565 (Feb. 1991).

Rottman, J.N., et al., "A Retinoic Acid–Responsive Element in the Apolipoprotein AI Gene Distinguishes Between Two Different Retinoid Acid Response Pathways", *Mol. Cell. Biol.* 11(7):3814–3820 (Jul. 1991).

Widom, R.L., et al., *Circulation: Abstracts from the 62nd Scientific Sessions of the American Heart Association, Nov. 13–16, 1989*, 80:II–465 (Oct. 1989).

Higuchi, K., et al., "Tissue–Specific Expression of Apolipoprotein A–I (ApoA–I), Is Regulated by the 5'–Flanking Region of the Human Apo–I Gene", *J. Biol. Chem.* 263(34):18,530–18,536 (Dec. 1988).

Sastry, K.N., et al., "Different cis–Acting DNA Elements Control Expression of the Human Apolipoprotein AI Gene in Different Cell Types", *Mol. Cell. Biol.*, 8(2):605–614 (Feb. 1988).

Ginsburg, G.S., and Karathanasis, S.K., *Circulation: Abstracts from the 62nd Scientific Sessions of the American Heart Association, Nov. 13–16, 1989* 80(4):II–465 (Oct. 1989).

Hardon, E.M., et al., "Two Distinct Factors Interact with the Promoter Regions of Several Liver–Specific Genes", *EMBO J.* 7(6):1711–1719 (1988).

Das, H.K., et al., "Cell Type–Specific Expression of the Human APOB Gene is Controlled by Two cis–Acting Regulatory Regions", *J. Biol. Chem.* 269(23):11,452–11,458 (Aug. 1988).

Ogami, K., et al., "Promoter Elements and Factors Required for Hepatic and Intestinal Transcription of the Human ApoCIII Gene", *J. Biol. Chem.* 265(17):9808–9815 (Jun. 1990).

*Primary Examiner*—David Guzo
*Attorney, Agent, or Firm*—Hamilton, Brook, Smith & Reynolds, P.C.

[57] ABSTRACT

Activation of the apolipoprotein AI (apoAI) gene in mammalian liver cells has been studied, as described herein, and shown to depend on synergistic interactions between nuclear proteins which bind to three distinct sites within a hepatocyte-specific transcriptional enhancer located between nucleotides –222 to –110 5' of the human apoAI gene (relative to the transcription start site). Two proteins, the apoAI regulatory protein-1 and the retinoic acid receptor RXRα, have been shown to regulate expression of the apoAI gene.

18 Claims, 8 Drawing Sheets

```
                    Site A
      -220     -210     -200     -190     -180
       .        .        .        .        .
      CCGCCCCCACTGAACCCTTGACCCCTGCCCTGCAGCCCCCGCA
      ------------------GG----------------------
      ------------------------------------------
      ------------------------------------------
      ------------------GG----------------------
      ------------------GG----------------------
      ------------------------------------------

Site B
         -170     -160     -150     -140
          .        .        .        .
         GCTTGCTGTTTGCCCACTCTATTTGCCCAGCCCCAGGGAC
         ------G-GGG--------GGGGG---------------
         ---------------------------------------
         ---------------------------------------
         ------G-GGG--------GGGGG---------------
         ------G-GGG--------GGGGG---------------
```

|  | Site C |  |  | % Activity |
|---|---|---|---|---|
|  | -130 | -120 | -110 |  |
|  | . | . | . |  |
|  | AGAGCTGATCCTTGAACTCTTAAGTTCCAC | | | 100.0 |
|  | ------------------------------ | | | 28.6 |
|  | ------------------------------ | | | 23.8 |
|  | ----------GG------------------ | | | 23.8 |
|  | ----------GG------------------ | | | 5.7 |
|  | ------------------------------ | | | 12.3 |
|  | ----------GG------------------ | | | 11.4 |
|  | pA10CATGem4 | | | 9.5 |

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 113 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: enhancer
        ( B ) LOCATION: 1..113
        ( D ) OTHER INFORMATION: /standard_name= "apolipoprotein AI enhancer"

( x i ) SEQUENCE DESCRIPTION: SEQ ID NO:1:

```
CCGCCCCCAC TGAACCCTTG ACCCCTGCCC TGCAGCCCCC GCAGCTTGCT GTTTGCCCAC        60
TCTATTTGCC CAGCCCCAGG GACAGAGCTG ATCCTTGAAC TCTTAAGTTC CAC              113
```

( 2 ) INFORMATION FOR SEQ ID NO:2:

( i ) SEQUENCE CHARACTERISTICS:
        ( A ) LENGTH: 113 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
CCGCCCCCAC TGAACCCGGG ACCCCTGCCC TGCAGCCCCC GCAGCTTGCT GTTTGCCCAC        60
TCTATTTGCC CAGCCCCAGG GACAGAGCTG ATCCTTGAAC TCTTAAGTTC CAC              113
```

( 2 ) INFORMATION FOR SEQ ID NO:3:

( i ) SEQUENCE CHARACTERISTICS:
        ( A ) LENGTH: 113 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
CCGCCCCCAC TGAACCCTTG ACCCCTGCCC TGCAGCCCCC GCAGCTTGCG GGGGGCCCAC        60
TCGGGGGGCC CAGCCCCAGG GACAGAGCTG ATCCTTGAAC TCTTAAGTTC CAC              113
```

( 2 ) INFORMATION FOR SEQ ID NO:4:

( i ) SEQUENCE CHARACTERISTICS:
        ( A ) LENGTH: 113 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:4:

```
CCGCCCCCAC TGAACCCTTG ACCCCTGCCC TGCAGCCCCC GCAGCTTGCT GTTTGCCCAC        60
TCTATTTGCC CAGCCCCAGG GACAGAGCTG ATCCGGGAAC TCTTAAGTTC CAC              113
```

( 2 ) INFORMATION FOR SEQ ID NO:5:

( i ) SEQUENCE CHARACTERISTICS:
        ( A ) LENGTH: 113 base pairs (B) TYPE: nucleic acid
(C) STRANDEDNESS: double
(D) TOPOLOGY: linear (xi) SEQUENCE DESCRIPTION: SEQ ID NO:5:

| | | | | | |
|---|---|---|---|---|---|
| CCGCCCCCAC | TGAACCCGGG | ACCCCTGCCC | TGCAGCCCCC | GCAGCTTGCT | GTTTGCCCAC | 60 |
| TCTATTTGCC | CAGCCCCAGG | GACAGAGCTG | ATCCGGGAAC | TCTTAAGTTC | CAC | 113 |

(2) INFORMATION FOR SEQ ID NO:6:

(i) SEQUENCE CHARACTERISTICS:
(A) LENGTH: 113 base pairs
(B) TYPE: nucleic acid
(C) STRANDEDNESS: double
(D) TOPOLOGY: linear (xi) SEQUENCE DESCRIPTION: SEQ ID NO:6:

| | | | | | |
|---|---|---|---|---|---|
| CCGCCCCCAC | TGAACCCGGG | ACCCCTGCCC | TGCAGCCCCC | GCAGCTTGCG | GGGGCCCAC | 60 |
| TCGGGGGCC | CAGCCCCAGG | GACAGAGCTG | ATCCTTGAAC | TCTTAAGTTC | CAC | 113 |

(2) INFORMATION FOR SEQ ID NO:7:

(i) SEQUENCE CHARACTERISTICS:
(A) LENGTH: 113 base pairs
(B) TYPE: nucleic acid
(C) STRANDEDNESS: double
(D) TOPOLOGY: linear (xi) SEQUENCE DESCRIPTION: SEQ ID NO:7:

| | | | | | |
|---|---|---|---|---|---|
| CCGCCCCCAC | TGAACCCTTG | ACCCCTGCCC | TGCAGCCCCC | GCAGCTTGCG | GGGGCCCAC | 60 |
| TCGGGGGCC | CAGCCCCAGG | GACAGAGCTG | ATCCGGGAAC | TCTTAAGTTC | CAC | 113 |

(2) INFORMATION FOR SEQ ID NO:8:

(i) SEQUENCE CHARACTERISTICS:
(A) LENGTH: 1748 base pairs
(B) TYPE: nucleic acid
(C) STRANDEDNESS: double
(D) TOPOLOGY: linear (ii) MOLECULE TYPE: cDNA to mRNA (ix) FEATURE:
(A) NAME/KEY: CDS
(B) LOCATION: 343..1584
(D) OTHER INFORMATION: /product="apolipoprotein AI regulatory protein-1"

(xi) SEQUENCE DESCRIPTION: SEQ ID NO:8:

| | | | | | |
|---|---|---|---|---|---|
| CTCCACGTTC | TGCTCCCACT | CGCTCTCCTG | TCCCCTTCCC | CTCCCCTCCC | GGCGGAAAGC | 60 |
| CCCCCGAAAC | CAACAAAGCT | GAGCCGAGAG | AAACAAACAA | AACAAACACA | CCGGGCCAGA | 120 |
| CAAGCCATCG | ACAAAACTTT | GCAAAAGCAA | AAACAAAAAA | GGAAAAACTA | ACCAACCTCA | 180 |
| ACCAACCAGC | CCCCGAGCCA | CCCGGGGCGC | CCTCCCGCGC | CCTCTTGCAC | CCTCGCACAC | 240 |
| ACAAAAGGCG | GCGCGCCGGA | GCCCGAGACC | CGGGGAGCCG | CCGCCGCCCC | GCCGCCGCCC | 300 |
| GCAGCCAGGG | GAGCAGGAAG | TCCGGACGCA | GCCCCCATAG | AT ATG GCA ATG GTA | | 354 |
| | | | | Met Ala Met Val | | |
| | | | | 1 | | |

| GTC | AGC | ACG | TGG | CGC | GAC | CCC | CAG | GAC | GAG | GTG | CCC | GGC | TCA | CAG | GGC | 402 |
|---|---|---|---|---|---|---|---|---|---|---|---|---|---|---|---|---|
| Val | Ser | Thr | Trp | Arg | Asp | Pro | Gln | Asp | Glu | Val | Pro | Gly | Ser | Gln | Gly | |
| 5 | | | | | 10 | | | | | 15 | | | | | 20 | |

| AGC | CAG | GCC | TCG | CAG | GCG | CCG | CCC | GTG | CCC | GGC | CCG | CCG | CCC | GGC | GCC | 450 |
|---|---|---|---|---|---|---|---|---|---|---|---|---|---|---|---|---|
| Ser | Gln | Ala | Ser | Gln | Ala | Pro | Pro | Val | Pro | Gly | Pro | Pro | Pro | Gly | Ala | |
| | | 25 | | | | | 30 | | | | | | 35 | | | |

| | | | | | | | | | | | | | | | | |
|---|---|---|---|---|---|---|---|---|---|---|---|---|---|---|---|---|
| CCG | CAC | ACG | CCA | CAG | ACG | CCC | GGC | CAA | GGG | GGC | CCA | GCC | AGC | ACG | CCA | 498 |
| Pro | His | Thr | Pro 40 | Gln | Thr | Pro | Gly | Gln 45 | Gly | Gly | Pro | Ala | Ser 50 | Thr | Pro | |
| GCC | CAG | ACG | GCG | GCC | GGT | GGC | CAG | GGC | GGC | CCT | GGC | GGC | CCG | GGT | AGC | 546 |
| Ala | Gln | Thr 55 | Ala | Ala | Gly | Gly | Gln 60 | Gly | Gly | Pro | Gly | Gly 65 | Pro | Gly | Ser | |
| GAC | AAG | CAG | CAG | CAG | CAG | CAA | CAC | ATC | GAG | TGC | GTG | GTG | TGC | GGA | GAC | 594 |
| Asp | Lys 70 | Gln | Gln | Gln | Gln | Gln 75 | His | Ile | Glu | Cys | Val 80 | Val | Cys | Gly | Asp | |
| AAG | TCG | AGC | GGC | AAG | CAC | TAC | GGC | CAG | TTC | ACG | TGC | GAG | GGC | TGC | AAG | 642 |
| Lys 85 | Ser | Ser | Gly | Lys | His 90 | Tyr | Gly | Gln | Phe | Thr 95 | Cys | Glu | Gly | Cys | Lys 100 | |
| AGC | TTC | TTC | AAG | CGC | AGC | GTG | CGG | AGG | AAC | CTG | AGC | TAC | ACG | TGC | CGC | 690 |
| Ser | Phe | Phe | Lys 105 | Arg | Ser | Val | Arg | Arg 110 | Asn | Leu | Ser | Tyr | Thr 115 | Cys | Arg | |
| GCC | AAC | CGG | AAC | TGT | CCC | ATC | GAC | CAG | CAC | CAT | CGC | AAC | CAG | TGC | CAG | 738 |
| Ala | Asn | Arg | Asn 120 | Cys | Pro | Ile | Asp | Gln 125 | His | His | Arg | Asn | Gln 130 | Cys | Gln | |
| TAC | TGC | CGC | CTC | AAA | AAG | TGC | CTC | AAA | GTG | GGC | ATG | AGA | CGG | GAA | GCG | 786 |
| Tyr | Cys | Arg 135 | Leu | Lys | Lys | Cys | Leu 140 | Lys | Val | Gly | Met | Arg 145 | Arg | Glu | Ala | |
| GTG | CAG | AGG | GGC | AGG | ATG | CCG | CCG | ACC | CAG | CCG | ACC | CAC | GGG | CAG | TTC | 834 |
| Val | Gln 150 | Arg | Gly | Arg | Met | Pro 155 | Pro | Thr | Gln | Pro | Thr 160 | His | Gly | Gln | Phe | |
| GCG | CTG | ACC | AAC | GGG | GAT | CCC | CTC | AAC | TGC | CAC | TCG | TAC | CTG | TCC | GGA | 882 |
| Ala 165 | Leu | Thr | Asn | Gly | Asp 170 | Pro | Leu | Asn | Cys | His 175 | Ser | Tyr | Leu | Ser | Gly 180 | |
| TAT | ATT | TCC | CTG | CTG | TTG | CGC | GCG | GAG | CCC | TAT | CCC | ACG | TCG | CGC | TTC | 930 |
| Tyr | Ile | Ser | Leu | Leu 185 | Leu | Arg | Ala | Glu | Pro 190 | Tyr | Pro | Thr | Ser | Arg 195 | Phe | |
| GGC | AGC | CAA | TGC | ATG | CAG | CCC | AAC | AAC | ATC | ATG | GGT | ATC | GAG | AAC | ATT | 978 |
| Gly | Ser | Gln | Cys 200 | Met | Gln | Pro | Asn | Asn 205 | Ile | Met | Gly | Ile | Glu 210 | Asn | Ile | |
| TGC | GAA | CTG | GCC | GCG | AGG | ATG | CTC | TTC | AGC | GCC | GTC | GAG | TGG | GCC | CGG | 1026 |
| Cys | Glu | Leu 215 | Ala | Ala | Arg | Met | Leu 220 | Phe | Ser | Ala | Val | Glu 225 | Trp | Ala | Arg | |
| AAC | ATC | CCC | TTC | TTC | CCC | GAC | CTG | CAG | ATC | ACG | GAC | CAG | GTG | GCC | CTG | 1074 |
| Asn | Ile 230 | Pro | Phe | Phe | Pro | Asp 235 | Leu | Gln | Ile | Thr | Asp 240 | Gln | Val | Ala | Leu | |
| CTT | CGC | CTC | ACC | TGG | AGC | GAG | CTG | TTT | GTG | TTG | AAT | GCG | GCG | CAG | TGC | 1122 |
| Leu 245 | Arg | Leu | Thr | Trp | Ser 250 | Glu | Leu | Phe | Val | Leu 255 | Asn | Ala | Ala | Gln | Cys 260 | |
| TCC | ATG | CCC | CTC | CAC | GTC | GCC | CCG | CTC | CTG | GCC | GCC | GCC | GGC | CTG | CAT | 1170 |
| Ser | Met | Pro | Leu | His 265 | Val | Ala | Pro | Leu | Leu 270 | Ala | Ala | Ala | Gly | Leu 275 | His | |
| GCT | TCG | CCC | ATG | TCC | GCC | GAC | CGG | GTG | GTC | GCC | TTT | ATG | GAC | CAC | ATA | 1218 |
| Ala | Ser | Pro | Met 280 | Ser | Ala | Asp | Arg | Val 285 | Val | Ala | Phe | Met | Asp 290 | His | Ile | |
| CGG | ATC | TTC | CAA | GAG | CAA | GTG | GAG | AAG | CTC | AAG | GCG | CTG | CAC | GTT | GAC | 1266 |
| Arg | Ile | Phe 295 | Gln | Glu | Gln | Val | Glu 300 | Lys | Leu | Lys | Ala | Leu 305 | His | Val | Asp | |
| TCA | GCC | GAG | TAC | AGC | TGC | CTC | AAG | GCC | ATA | GTC | CTG | TTC | ACC | TCA | GAT | 1314 |
| Ser | Ala 310 | Glu | Tyr | Ser | Cys | Leu 315 | Lys | Ala | Ile | Val | Leu 320 | Phe | Thr | Ser | Asp | |
| GCC | TGT | GGT | CTC | TCT | GAT | GTA | GCC | CAT | GTG | GAA | AGC | TTG | CAG | GAA | AAG | 1362 |
| Ala 325 | Cys | Gly | Leu | Ser | Asp 330 | Val | Ala | His | Val | Glu 335 | Ser | Leu | Gln | Glu | Lys 340 | |
| TCT | CAG | TGT | GCT | TTG | GAA | GAA | TAC | GTT | AGG | AGC | CAG | TAC | CCC | AAC | CAG | 1410 |
| Ser | Gln | Cys | Ala | Leu 345 | Glu | Glu | Tyr | Val | Arg 350 | Ser | Gln | Tyr | Pro | Asn 355 | Gln | |

```
CCG  ACG  AGA  TTC  GGA  AAG  CTT  TTG  CTT  CGC  CTC  CCT  TCC  CTC  CGC  ACC    1458
Pro  Thr  Arg  Phe  Gly  Lys  Leu  Leu  Leu  Arg  Leu  Pro  Ser  Leu  Arg  Thr
          360                      365                     370

GTC  TCC  TCC  TCA  GTC  ATA  GAG  CAA  TTG  TTT  TTC  GTC  CGT  TTG  GTA  GGT    1506
Val  Ser  Ser  Ser  Val  Ile  Glu  Gln  Leu  Phe  Phe  Val  Arg  Leu  Val  Gly
          375                      380                     385

AAA  ACC  CCC  ATC  GAA  ACC  CTC  ATC  CGG  GAT  ATG  TTA  CTG  TCC  GGC  AGC    1554
Lys  Thr  Pro  Ile  Glu  Thr  Leu  Ile  Arg  Asp  Met  Leu  Leu  Ser  Gly  Ser
          390                      395                     400

AGT  TTT  AAC  TGG  CCG  TAT  ATG  GCA  ATT  CAA  TAAATAAATA AAATAAGAAG            1604
Ser  Phe  Asn  Trp  Pro  Tyr  Met  Ala  Ile  Gln
405                      410

GGGGAGTGAA ACAGAGAAAG AAAAGGCAAA AGACTGGTTT GTTTGCTTAA TTTCCTTCTG                  1664

TTAAGAAAGG ATATAAAAGG ATGTTACAAG TTTGCTAAAA GAAGAGAGGG GAAGAATTTA                  1724

ATGGACTGTG AATTTCAAAA AAAA                                                         1748
```

( 2 ) INFORMATION FOR SEQ ID NO:9:

( i ) SEQUENCE CHARACTERISTICS:
        ( A ) LENGTH: 414 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met  Ala  Met  Val  Val  Ser  Thr  Trp  Arg  Asp  Pro  Gln  Asp  Glu  Val  Pro
 1              5                       10                      15

Gly  Ser  Gln  Gly  Ser  Gln  Ala  Ser  Gln  Ala  Pro  Pro  Val  Pro  Gly  Pro
               20                       25                      30

Pro  Pro  Gly  Ala  Pro  His  Thr  Pro  Gln  Thr  Pro  Gly  Gln  Gly  Gly  Pro
          35                       40                       45

Ala  Ser  Thr  Pro  Ala  Gln  Thr  Ala  Ala  Gly  Gly  Gln  Gly  Gly  Pro  Gly
     50                       55                       60

Gly  Pro  Gly  Ser  Asp  Lys  Gln  Gln  Gln  Gln  His  Ile  Glu  Cys  Val
 65                  70                       75                      80

Val  Cys  Gly  Asp  Lys  Ser  Ser  Gly  Lys  His  Tyr  Gly  Gln  Phe  Thr  Cys
               85                       90                      95

Glu  Gly  Cys  Lys  Ser  Phe  Phe  Lys  Arg  Ser  Val  Arg  Arg  Asn  Leu  Ser
               100                      105                     110

Tyr  Thr  Cys  Arg  Ala  Asn  Arg  Asn  Cys  Pro  Ile  Asp  Gln  His  His  Arg
               115                      120                     125

Asn  Gln  Cys  Gln  Tyr  Cys  Arg  Leu  Lys  Lys  Cys  Leu  Lys  Val  Gly  Met
     130                      135                      140

Arg  Arg  Glu  Ala  Val  Gln  Arg  Gly  Arg  Met  Pro  Pro  Thr  Gln  Pro  Thr
145                      150                      155                     160

His  Gly  Gln  Phe  Ala  Leu  Thr  Asn  Gly  Asp  Pro  Leu  Asn  Cys  His  Ser
                    165                      170                     175

Tyr  Leu  Ser  Gly  Tyr  Ile  Ser  Leu  Leu  Leu  Arg  Ala  Glu  Pro  Tyr  Pro
               180                      185                     190

Thr  Ser  Arg  Phe  Gly  Ser  Gln  Cys  Met  Gln  Pro  Asn  Asn  Ile  Met  Gly
          195                      200                      205

Ile  Glu  Asn  Ile  Cys  Glu  Leu  Ala  Ala  Arg  Met  Leu  Phe  Ser  Ala  Val
     210                      215                      220

Glu  Trp  Ala  Arg  Asn  Ile  Pro  Phe  Phe  Pro  Asp  Leu  Gln  Ile  Thr  Asp
225                      230                      235                     240
```

-continued

| | | | | | | | | | | | | | | | |
|---|---|---|---|---|---|---|---|---|---|---|---|---|---|---|---|
| Gln | Val | Ala | Leu | Leu 245 | Arg | Leu | Thr | Trp | Ser 250 | Glu | Leu | Phe | Val | Leu 255 | Asn |
| Ala | Ala | Gln | Cys 260 | Ser | Met | Pro | Leu | His 265 | Val | Ala | Pro | Leu | Leu 270 | Ala | Ala |
| Ala | Gly | Leu 275 | His | Ala | Ser | Pro | Met 280 | Ser | Ala | Asp | Arg | Val 285 | Val | Ala | Phe |
| Met | Asp 290 | His | Ile | Arg | Ile | Phe 295 | Gln | Glu | Gln | Val | Glu 300 | Lys | Leu | Lys | Ala |
| Leu 305 | His | Val | Asp | Ser | Ala 310 | Glu | Tyr | Ser | Cys | Leu 315 | Lys | Ala | Ile | Val | Leu 320 |
| Phe | Thr | Ser | Asp | Ala 325 | Cys | Gly | Leu | Ser | Asp 330 | Val | Ala | His | Val | Glu 335 | Ser |
| Leu | Gln | Glu | Lys 340 | Ser | Gln | Cys | Ala | Leu 345 | Glu | Glu | Tyr | Val | Arg 350 | Ser | Gln |
| Tyr | Pro | Asn 355 | Gln | Pro | Thr | Arg | Phe 360 | Gly | Lys | Leu | Leu | Leu 365 | Arg | Leu | Pro |
| Ser | Leu 370 | Arg | Thr | Val | Ser | Ser 375 | Ser | Val | Ile | Glu | Gln 380 | Leu | Phe | Phe | Val |
| Arg 385 | Leu | Val | Gly | Lys | Thr 390 | Pro | Ile | Glu | Thr | Leu 395 | Ile | Arg | Asp | Met | Leu 400 |
| Leu | Ser | Gly | Ser | Ser 405 | Phe | Asn | Trp | Pro | Tyr 410 | Met | Ala | Ile | Gln | | |

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

TGAACCTTGC CTAGGG        16

( 2 ) INFORMATION FOR SEQ ID NO:11:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

CTGATTGCCC A        11

METHODS OF SCREENING FOR COMPOUNDS WITH ABILITY TO ALTER APOLIPOPROTEIN AI GENE EXPRESSION

RELATED APPLICATION

This application is a division of application Ser. No. 08/142,838 filed Oct. 25, 1993, abandoned, which is File Wrapper continuation application of U.S. Ser. No. 07/784, 472, filed Oct. 24, 1991 (abandoned), which is a continuation-in-part application of U.S. Ser. No. 07/645, 139, filed Jan. 24, 1991 (abandoned).

GOVERNMENT SUPPORT

Work leading to this invention was supported by Grant No. HL32032 from the National Institutes of Health and by the American Heart Association. The U.S. government has certain rights to this invention.

BACKGROUND OF THE INVENTION

Apolipoprotein AI (apoAI) is a major protein constituent of high-density lipoproteins (HDL) and chylomicrons. HDL particles are essential for reverse cholesterol transport, the process by which cholesterol is transported from extrahepatic tissues to the liver for excretion (Gomset, *J. Lipid Res.*, 9:155–167 (1968)). Chylomicrons transport dietary cholesterol and other lipids, including retinyl esters, to the liver (Goodman and Blaner, in *The Retinoids*, Vol. 2 V. Sporn et al. (Eds.) V. Academic Press, Orlando. Fla. (1984)). The apoAI gene is expressed primarily in liver and intestine, and it is regulated by developmental, dietary and hormonal factors (Elshourbagy et al., *Proc. Natl. Acad. Sci. USA*, 82:8242–8246; Haddad et al., *J. Biol. Chem.*, 161:13268–13277 (1986)).

The accumulation and utilization of cholesterol by tissues are dependent on a dynamic balance between the mechanisms that determine the rates of de novo cholesterol synthesis, the rates of synthesis and hydrolysis of stored pools of cholesteryl esters, and the rates of uptake and removal of cholesterol from cells by plasma lipoproteins. Removed cholesterol binds to a species of HDL particles containing primarily apoAI. After its esterification by lecithin:cholesterol acetyltransferase (LCAT; an enzyme activated by apoAI), cholesterol is transported to the liver, where it is excreted either directly or in the form of bile acids. The critical role of HDL and apoAI in cholesterol homeostasis, in particular in preventing deposition of excessive amounts of cholesterol in coronary and other arteries, is exemplified by epidemiological and genetic evidence indicating a strong correlation between decreased HDL and apoAI plasma levels and the development of atherosclerotic heart disease. Thus, the recent observation that there is a direct correlation between apoAI plasma levels and hepatic apoAI mRNA concentrations (Sorci-Thomas, M. et al., *J. Biol. Chem.*, 263:5183–5189 (1988); Sorci-Thomas, M. et al., *J. Lipid Res.*, 30:1397–1403 (1989)) suggests that factors controlling expression of the apoAI gene in liver could play an important role in tissue cholesterol accumulation and atherosclerosis.

SUMMARY OF THE INVENTION

This invention pertains to methods for regulating the expression of an apolipoprotein gene and to methods for regulating cholesterol accumulation and disease/damage caused thereby. The invention is based upon the discovery that activation of the apolipoprotein AI (apoAI) gene in mammalian liver cells depends on synergistic interactions between nuclear proteins that bind to three distinct sites (denoted herein as Sites A, B and C) within a hepatocyte-specific transcriptional enhancer located between nucleotides −222 to −110 in the apoAI gene 5'-flanking region. Each site is inactive on its own and does not activate transcription when it is individually multimerized or when it is combined with other protein-binding sites present in the simian virus 40 (SV40) early promoter. Results described herein indicate that protein-protein interactions between transcription factors bound to the three sites within the apoAI gene enhancer couple this enhancer to the basic transcription machinery.

The present invention also pertains to a protein which regulates apoAI gene expression and is a novel member of the steroid hormone receptor superfamily. This protein, referred to herein as apoAI regulatory protein-1 (ARP-1), binds specifically to Site A of the apoAI hepatocyte-specific enhancer. ARP-1 is a protein of 414 amino acid residues and has a molecular weight of approximately 47 kD. It binds to the regulatory element of the apoAI gene as a dimer. As described herein, it has been shown that ARP-1 represses apoAI gene expression under some conditions, but activates the gene under other conditions. For example, ARP-1 has been shown to downregulate apoAI gene expression in cotransfection experiments. Further, when ARP-1 binds the apoAI gene in combination with (as one component of a dimer with) the retinoic acid receptor RXRα, the apoAI gene in liver cells is repressed in the absence of retinoic acid. However, when the ARP-1/RXRα dimer binds in the presence of retinoic acid, the apoAI gene is activated. The involvement of novel steroid receptors in apolipoprotein gene regulation provides new approaches to the control of cholesterol metabolism. For example, ARP-1 can be used to regulate apolipoprotein gene expression and can play an important role in lipid metabolism and cholesterol homeostasis.

A retinoic acid response element in the upstream region of the apoAI gene has also been identified and shown to respond preferentially to the RXRα receptor, which is a retinoic acid responsive transcription factor. As described herein, binding of RXRα to Site A is enhanced by retinoic acid, and expression of apoAI gene constructs is upregulated by retinoic acid in the presence of RXRα. These results suggest that RXRα may play a role in regulation of cholesterol and retinoid metabolism, and that retinoids or other similar compounds could play an important role in regulating the apoAI gene and, thus, cellular cholesterol homeostasis.

BRIEF DESCRIPTION OF THE DRAWINGS

FIG. 4 shows plasmid constructs with the CAT gene under the control of the SV40 early promoter and either a fragment containing the −222 to −110 apoAI 5'-flanking region (its nucleotide sequence, SEQ ID NO:1 is shown) or several identical fragments containing nucleotide substitutions (indicated; SEQ ID NO:2–7) that eliminate nuclear protein binding to the corresponding binding sites. Plasmids were tested for CAT activity by transfection into HepG2 cells. All of the substituted fragments were cloned adjacent to and in the same transcriptional orientation with the SV40 early promoter.

FIGS. 5A–5B shows the nucleotide SEQ ID NO:8 and derived amino acid sequence (SEQ ID NO:9) of the ARP-1 cDNA clone λHP-16. Numbers of the left and right indicate nucleotide and amino acid residues, respectively. Abbreviations for the amino acids are A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr. The λHP-1 insert is shown between arrows. A termination codon upstream of the initiator ATG is underlined. A 66-amino acid region that corresponds to the DNA binding domain of the steroid receptors is boxed, and cysteines implicated in formation of Zn fingers are circled. Three overlapping consensus polyadenylation signals are bracketed. A pentanucleotide (ATTTA) implicated in regulation of mRNA stability is enclosed in a dashed box.

DETAILED DESCRIPTION OF THE INVENTION

Figure 1:
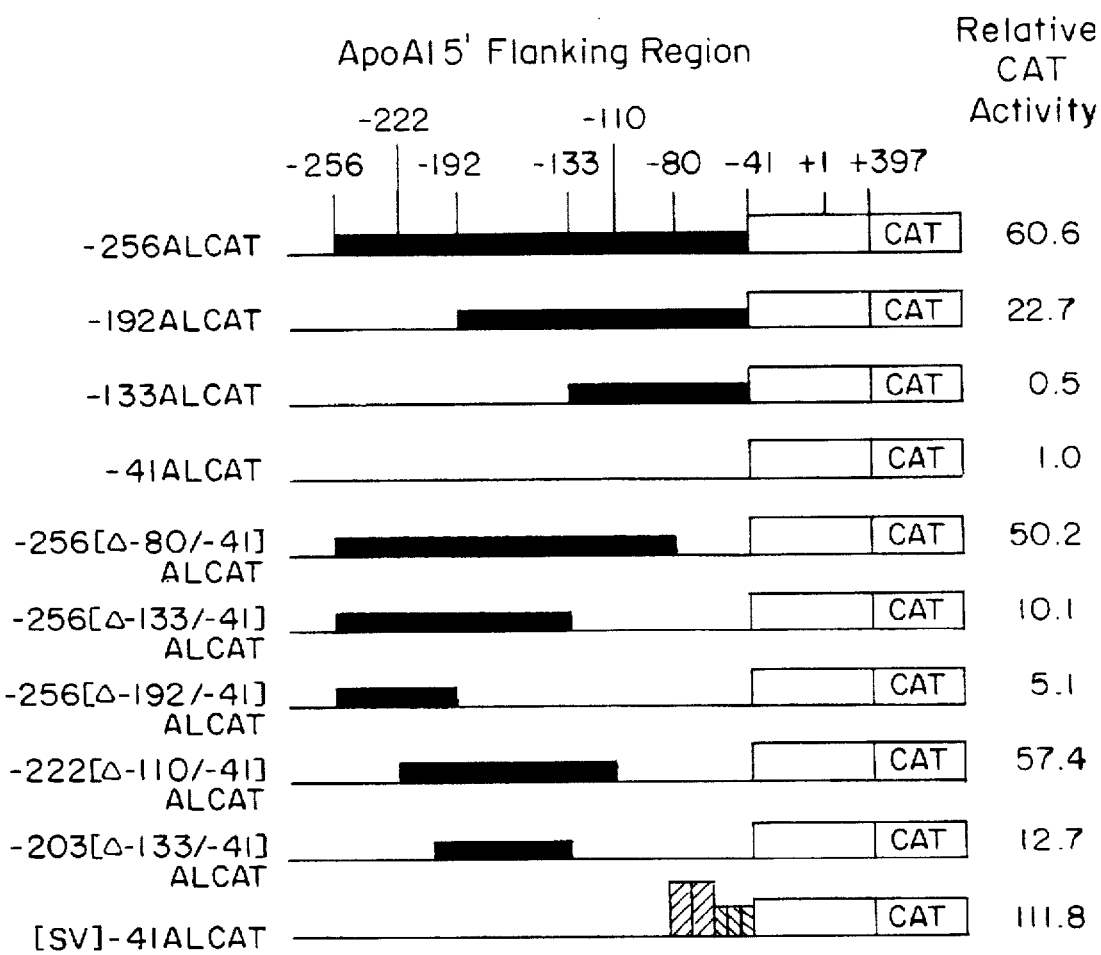
FIG. 1 illustrates the expression of apoAI-CAT fusion genes in hepatoma HepG2 cells. Plasmid constructs with the CAT gene (indicated) under the control of: the −41 to +397 apoAI gene region (open box); several DNA fragments spanning different portions of the −256 to −41 apoAI 5'-flanking region (filled box); or the SV40 enhancer with its 72-bp repeats (large hatched boxes) and 21-bp repeats (small hatched boxes); were tested for CAT activity by transient transfection into HepG2 cells. Each construct (25 µg) was cotransfected with plasmid pRSV-β-gal (5 µg; Edlund, T. et al., *Science*, 230:912–916 (1985)) to correct for variations in DNA uptake by the cells.

Activation of the apolipoprotein AI (apoAI) gene in mammalian liver cells has been studied, as described herein, and shown to depend on synergistic interactions between nuclear proteins which bind to three distinct sites within a hepatocyte-specific transcriptional enhancer located between nucleotides −222 to −110 upstream (5') of the human apoAI gene (relative to the apoAI gene transcription start site; SEQ ID NO:1). This region has been shown to be necessary and sufficient for expression of the apoAI gene in HepG2 cells and a powerful hepatocyte-specific transcriptional enhancer. It has also been shown that liver cells contain nuclear proteins that bind to three specific sites within the enhancer, A (−214 to −192; 9–31 of SEQ. ID NO:1), B (−169 to −146), and C (−134 to −119; 89–104 of SEQ ID NO:1), and that proteins bound to these sites act synergistically to stimulate enhancer activity. Occupation of all three of these sites by proteins is essential for maximal activity. Occupation of any two sites results in dramatically reduced activity. Occupation of any single site is not sufficient for activity.

Sites A, B, and C have no significant activity on their own, even when they are individually multimerized. However, their combination, as it occurs in the apoAI gene enhancer, results in very high levels of activity.

As further described herein, multiple proteins can bind to each of Sites A, B, and C. As a result, several different combinations of these proteins on the apoAI gene enhancer are possible. It is therefore conceivable, that alterations in the intracellular concentration of one or more of these proteins would favor one combination over the others, which could alter the transcriptional activity of the enhancer. The involvement of a complex network of multiple proteins that bind to apoAI gene enhancer could generate at least a part of the versatility of transcriptional control required for the diversity of expression of the apoAI gene during development and in response to dietary and hormonal factors.

A protein, designated apoAI regulatory protein-1 or ARP-1, has also been identified, and a cDNA clone for it has been isolated. ARP-1 binds to regulatory elements of the apoAI gene, as well as to a thyroid hormone-response element and to regulatory regions of the apoB, apoCIII, insulin and ovalbumin genes. ARP-1 is a new member of the steroid hormone receptor family and has a molecular weight of approximately 47 kD. It has been shown to bind to DNA as a dimer and to include a dimerization domain localized to its COOH-terminal region. In cotransfection studies, ARP-1 downregulates the apoAI gene, but it does not seem to function as a direct repressor, and its effects on transcription may depend on the promoter context in which it acts. As described herein, it has been shown that binding of positive regulators to Site A of the apoAI gene is essential for maximal levels of expression in HepG2 cells. An additional nuclear receptor, RXRα, has been shown to bind to Site A and activate transcription of apoAI, indicating that this site is responsive to both positive and negative regulatory proteins. Interaction among these factors could result in induction or repression of the apoAI gene in response to various signals. It is known that large amounts of dietary fat and cholesterol significantly reduce hepatic apoAI mRNA, raising the possibility that ARP-1 and RXRα may participate in mediating such effects. In addition, that these regulators could influence apolipoprotein concentrations suggests that they may have a key role in signal transduction mechanisms contributing to cholesterol homeostasis.

Further described herein is a retinoic acid response element identified in the upstream regulatory region of the human apoAI gene. This apoAI gene element has been shown to have a clearly preferential response to the recently identified nuclear retinoid receptor designated RXRα, in comparison with the receptors RARα and RARβ. As described, expression of the apoAI gene may be responsive to retinoid, as suggested by demonstration that apoAI gene constructs can be upregulated in HepG2 cells by retinoic acid in the presence of RXRα. The finding that the apoAI gene Site A is a functional RARE taken together with the previous observation that Site A is a positive response element for the recently cloned transcription factor HNF4, which is also a member of the steroid-thyroid hormone receptor superfamily (Sladek, F. M. et al., *Genes Dev.*, 4:2353-2365 (1990)), and the observation that Site A within the context of the apoAI gene promoter-enhancer functions as a negative response element for Arp-1 and Ear-3/COUP-TF strongly suggest that multiple regulatory signals converge onto this site to modulate apoAI gene expression. It is therefore reasonable to speculate that the level of apoAI gene expression is determined by the intracellular balance of all these signal transduction pathways. Indeed, in preliminary experiments it was observed that the negative effect of Arp-1 or Ear-3/COUP-TF on apoAI gene expression in HepG2 cells is overcome by overexpression of RXRα in the presence of retinoic acid.

These observations raise the possibility that retinoids, or other similar small hydrophobic molecules, play an important role in regulation of apoAI gene expression and suggest that such ligands are fundamental to the signal transduction mechanisms contributing to cholesterol and vitamin A transport and homeostasis. Moreover, these observations raise the intriguing possibility that such molecules acting via these signal transduction pathways are ultimately influencing processes involved in the initiation, progression, and severity of coronary heart disease.

The following is a detailed description of apoAI gene activation in mammalian liver cells, the ARP-1 protein and its function, the retinoic acid response element (RARE) present in the human apoAI gene upstream regulatory region, and applications of the findings described, such as in regulation of cholesterol and lipid metabolism, diagnosis of an individual's cholesterol or lipid metabolic capability or condition and hepatocyte-specific expression of a desired nucleic acid (DNA or RNA) sequence.

apoAI Gene Activation

The -222 to -110 apoAI gene region drives expression of the apoAI gene in HepG2 cells.

Work carried out to further delineate the regulatory elements present within the -256 to -41 5'-flanking region of the apoAI gene, which is known to be necessary and sufficient to direct liver-specific expression, showed that nearly all (greater than 90%) of the activity is mediated by sequences within the -222 to -110 DNA region (SEQ ID NO:1).

Previous experiments with cultured human hepatoma HepG2 cells (Higuchi, K. et al., *J. Biol. Chem.*, 263:18530-18536 (1988); Sastry, K. N. et al. *Mol. Cell. Biol.*, 8:605-614 (1988)) and transgenic mice (Walsh, A. et al., *J. Biol. Chem.*, 264:6488-6494 (1989)) have shown that sequences within the -256 to -41 apoAI gene 5'-flanking region are necessary and sufficient to direct liver-specific expression. To further delineate the regulatory elements present within this region, several 5' and 3' deletions of the -256 to -41 DNA fragment were prepared and inserted 41 nucleotides upstream from the transcription start site of the apoAI gene in a vector which contains the -41 to +397 apoAI gene region fused in the same transcriptional orientation with the bacterial CAT gene (vector -41ALCAT; Sastry, K. N. et al. *Mol. Cell. Biol.*, 8:605-614 (1988)). The resulting plasmid constructs (FIG. 1) were transiently transfected into HepG2 cells; the CAT enzymatic activity in these cells was determined, corrected for variations in DNA uptake by the cells, and compared with the corrected CAT activity of the vector -41ALCAT (FIG. 1). Consistent with previous observations (Sastry, K. N. et al. *Mol. Cell. Biol.*, 8:605-614 (1988)), the CAT activity of the construct containing the intact -256 to -41 DNA fragment (construct -256AI.CAT) was 60.6 times greater than that of a construct without any apoAI 5'-flanking region (-41ALCAT) and approximately half the activity of a similar construct containing the SV40 enhancer instead of the -256 to -41 DNA fragment (construct [SV]-41ALCAT). Deletion of the 5' sequences from -256 to -192 (construct -192ALCAT) resulted in CAT activity only 22.7 times greater than that of -41ALCAT, while further deletion to nucleotide -133 resulted in activity very similar to that of -41ALCAT. Deletion of 3' sequences from -41 to -80 (construct -256 [Δ-80/-41]ALCAT) resulted in CAT activity 50.2 times greater than that of -41ALCAT, while further deletions to nucleotides -133 (construct -256[Δ-133/-41ALCAT) and -192 (construct -256[Δ-192/-41]AI.CAT) resulted in activities 10.1 and 5.1 times greater, respectively, than that of -41ALCAT.

Similar experiments using DNA fragments spanning different internal regions of the -256 to -41 apoAI 5'-flanking region showed that the CAT activity of a construct containing a fragment that spans the -203 to -133 DNA region (construct -203[Δ-133/-41]ALCAT) was only 12.7 times greater than that of -41ALCAT (FIG. 1). The CAT activity levels obtained with the vector -41ALCAT and its derivative constructs reflect rates of transcription initiation from the authentic apoAI gene transcription start site (Sastry, K. N. et al., *Mol. Cell. Biol.*, 8:605-614 (1988)).

These results indicate that sequences within the -110 to -41 DNA region contribute very little to the activity of the -256 to -41 apoAI 5'-flanking region in HepG2 cells, and that nearly all (greater than 90%) of this activity is mediated by sequences within the -222 to -110 DNA region (SEQ ID NO:1).

The -222 to -110 apoAI gene region functions as a hepatocyte-specific transcriptional enhancer.

The enhancer activity of the -222 to -110 apoAI DNA fragment was shown, as described below, to be hepatocyte specific.

Figure 2:
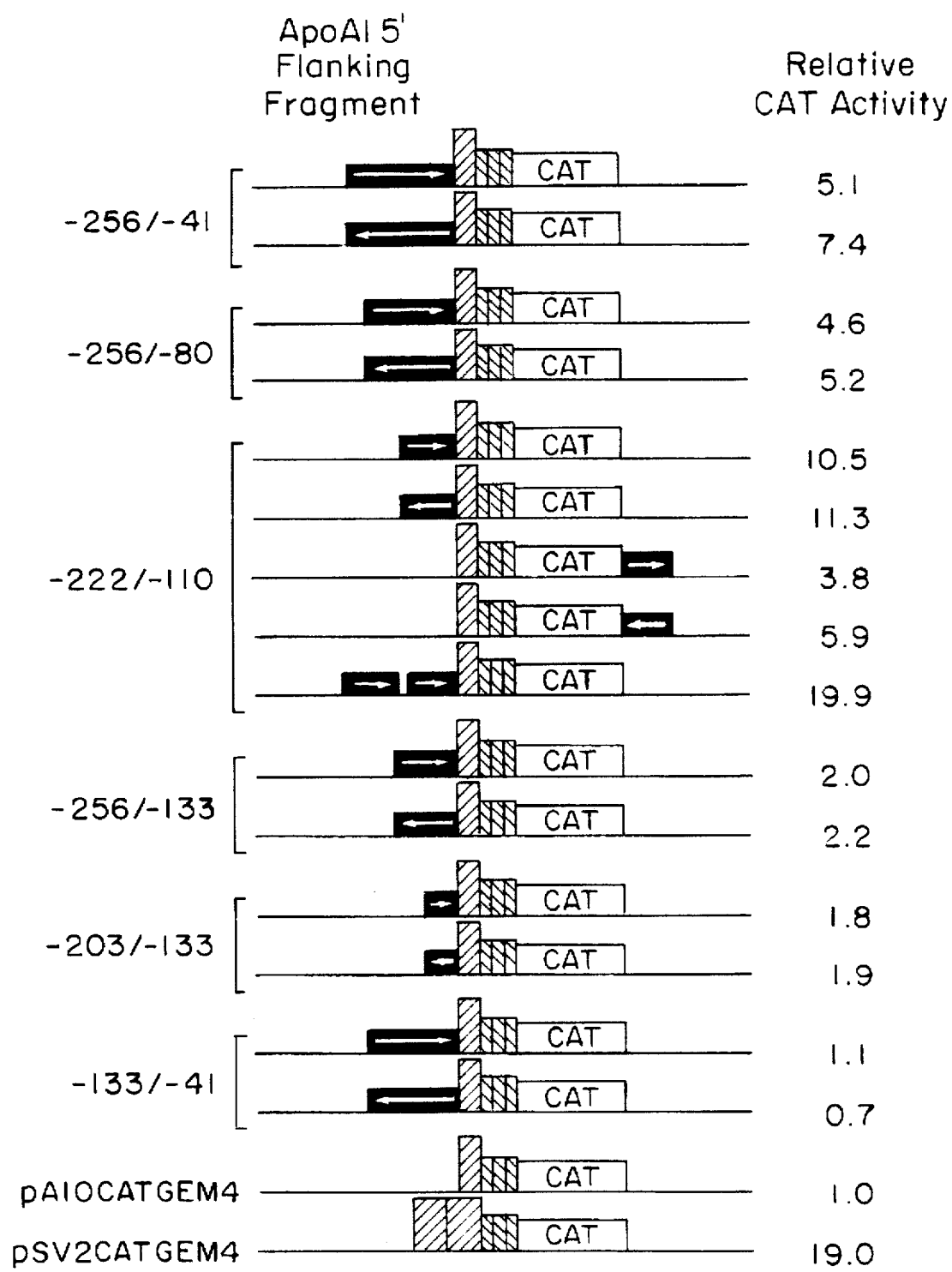
FIG. 2 illustrates the expression of the CAT gene under the control of the SV40 early promoter and different DNA fragments from the apoAI gene 5'-flanking region. Plasmid constructs with the CAT gene (indicated) under the control of the SV40 early promoter (hatched boxes; see also FIG. 1) and several DNA fragments spanning different portions of the −256 to −41 apoAI gene 5'-flanking region (filled boxes; arrows indicate the orientation of these fragments relative to apoAI gene transcription) were tested for CAT activity by transfection into HepG2 cells.

The finding that nearly all of the transcriptional activity of the -256 to -41 apoAI 5'-flanking region in HepG2 cells is mediated by sequences within the -222 to -110 DNA region, (SEQ ID NO:1) together with the previous observation that the -238 to -41 apoAI fragment functions as a hepatoma cell-specific transcriptional enhancer (Sastry, K. N. et al., *Mol. Cell. Biol.*, 8:605-614 (1988)), raised the possibility that this specific enhancer activity resides within the -222 to -110 DNA region. To evaluate this possibility, several DNA fragments spanning different portions of the -256 to -41 apoAI 5'-flanking region were inserted in both orientations adjacent to the SV40 early promoter in a CAT expression vector which contains the SV40 early promoter (without its enhancer) fused in the same transcriptional orientation with the CAT gene (vector pA10CATGEM4). The resulting constructs were used for CAT expression assays in HepG2 cells. CAT enzymatic activities in these cells were compared with the activity of the enhancerless vector pA10CATGEM4. The CAT activities of constructs containing the -256 to -41, -256 to -80, and -222 to -110 DNA fragments were 5.1 to 11.3 times greater than that of pA10CATGEM4, while the activities of constructs containing the -256 to -133, -203 to -133, and -133 to -42 fragments were very similar to that of pA10CATGEM4 (FIG. 2). Furthermore, the CAT activities of constructs containing the -222 to -110 DNA fragment distal to the SV40 early promoter (i.e., adjacent to the 3' end of the CAT gene) were 3.8 to 5.9 times greater than that of pA10CATGEM4. In addition, the CAT activities of constructs containing two copies of the −222 to −110 DNA fragment adjacent to the SV40 early promoter were approximately twice that of the construct containing a single copy and nearly identical to that of a similar construct containing the SV40 enhancer instead of the −222 to −110 DNA fragment (construct pSV2CATGEM4).

Thus, the activity of the single-copy −222 to −110 DNA fragment was approximately half of that of the SV40 enhancer, irrespective of whether transcription was initiated by the apoAI TATA box (compare the relative CAT activities of constructs −222[Δ−110/−41]AI.CAT and [SV]−41AI.CAT in FIG. 1) or the SV40 early promoter (FIG. 2). The difference in the magnitude of the relative CAT activity of construct −222[Δ−110/−41]AI.CAT compared with that of the construct containing the −222 to −110 apoAI gene fragment adjacent to the SV40 promoter (FIG. 2) reflects the higher basal activity of the SV40 early promoter compared with construct −41AI.CAT, both of which were used to determine the relative CAT activities values.

To determine whether the enhancer activity of the −222 to −110 DNA fragment, like that of the −238 to −41 DNA fragment (Sastry, K. N. et al., Mol. Cell. Biol., 8:605–614 (1988)), is hepatocyte specific, the constructs containing one or two copies of the −222 to −110 DNA fragment adjacent to the SV40 early promoter in pA10CATGEM4 were used for CAT expression assays by transient transfection into HepG2 cells and several other cultured cell types derived from various nonhepatic tissues. For each cell type, CAT activities were compared with the activity of the enhancerless construct pA10CATGEM4. In contrast to HepG2 cells, in which the activities of the constructs containing the −22 to −110 DNA fragment were comparable to that of the construct containing the SV40 enhancer (i.e., pSV2CATGEM4), in all other cell types the activities of these constructs were similar to the basal activity of the enhancerless construct pA10CATGEM4 (Table 1). Analogous results have been obtained for several other cultured cells of hepatic and nonhepatic tissue origin.

TABLE 1

Transcriptional Activity of the apoAI Gene Enhancer in Different Cell Types*

| | Relative CAT activity | | | | |
|---|---|---|---|---|---|
| Construct | HepG2 | Caco-2 | NIH3T3 | C2 myoblasts | HeLa |
| pSV2CATGEM4 | 19 | 360 | 10 | 42 | 64 |
| pA10CATGEM4 | 1 | 1 | 1 | 1 | 1 |
| −222 to −110 | 11 | 1.7 | 1 | 1 | 0.7 |
| 2 × −222 to −110 | 20 | 4.8 | 1 | 1 | 2 |

*Plasmid constructs containing one (−222 to −110) or two (2 × −222 to −110) copies of the apoAI gene enhancer adjacent to and in the same transcriptional orientation with the SV40 early promoter in the vector pA10CATGEM4 (see FIG. 2) and the constructs pA10CATGEM4 and pSV2CATGEM4 were tested for CAT activity by transient transfection into the indicated cell types.

These results indicate that the hepatocyte-specific enhancer activity of the −238 to −41 apoAI gene fragment is mediated by sequences within the −222 to −110 DNA region, (SEQ ID NO:1) and, together with the results discussed above, suggest that the sequences directing liver-specific expression of the apoAI gene are colocalized with the sequences mediating hepatocyte-specific enhancer activity. Furthermore, the observation that the enhancer activities of the −256 to −41, −256 to −80, and −222 to −110 DNA fragments are greater than the sum of the activities of the −256 to −133 and −133 to −41 fragments suggests that DNA elements 5' and 3' to nucleotide position −133 function together to generate this enhancer activity. Moreover, the observation that two copies of the −222 to −110 fragment mediate twice the enhancer activity of a single copy raises the possiblity that transcription factors in HepG2 cells interact with sequences within this fragment, and that the local concentration of these factors influences the rate of transcription initiation of the apoAI gene. The absence of enhancer activity of the −222 to −110 DNA fragment in intestinal carcinoma (Caco-2) cells, which express high levels of apoAI mRNA (Sastry, K. N. et al., Mol. Cell. Biol., 8:605–614 (1988)), indicates that the enhancer activity of this fragment is strictly hepatocyte cell specific, and suggests that transcription activation of the apoAI gene in the intestine is most likely mediated by alternative transcription activation pathways.

Nuclear proteins in HepG2 cells bind to distinct sites within the apoAI gene enhancer.

The transcriptional activity of the −222 to −110 apoAI gene fragment in hepatocytes raises the possibility that these cells contain transcriptional factors that bind to sequences within this fragment and increase the rate of productive transcription initiation events on the apoAI gene promoter. Experiments carried out to identify such factors showed that nuclear proteins in HepG2 cells bind to sequences within three distinct sites, A (−214 to −192; 9–31 of SEQ ID NO:1), B (−169 to −146), and C (−134 to −119; 89–104 of SEQ ID NO:1), in the apoAI gene enhancer (FIG. 3), and that protein binding to each of these sites is independent of protein binding to the others. Furthermore, these results suggest that the same or very similar proteins bind to Sites A and C, and that a different protein binds to Site B.

A search for these factors was initially carried out by gel retardation assays using HepG2 cell nuclear extracts and the −222 to −110 DNA fragment as a probe. Incubation of these extracts with the probe resulted in formation of retardation complexes that was inhibited in a competition experiment by a 50-fold or greater molar excess of unlabeled −222 to −110 DNA fragment, but not by a 500-fold molar excess of HindIII-digested bacteriophage λ DNA or several other DNA fragments, including the SV40 and cytomegalovirus enhancers, the Rous sarcoma virus long terminal repeat, and a fragment containing the entire human apoAI gene from nucleotide position −42 to the 314th nucleotide 3' of the polyadenylation signal. Control experiments indicated that treatment of the extracts with 0.1% SDS or 50 µg per ml of Proteinase K completely eliminated formation of these complexes, while heating of the extracts at 65° C. for 10 min resulted in complexes with greater electrophoretic mobility. Thus, it appears that multiple nuclear proteins, some of which are heat resistant, bind to the apoAI gene enhancer. Gel retardation assays using as probes three restriction fragments spanning the −222 to −189, −188 to −146, and −145 to −110 regions showed that each of these fragments formed sequence-specific retardation complexes with HepG2 cell nuclear extracts.

More precise mapping of the nucleotide sequences involved in these DNA-protein interactions was carried out by DNase I protection assays using the −256 to −80 apoAI gene fragment as a probe. HepG2 nuclear proteins protected the following nucleotide regions from digestion by DNase I: −214 to −192, −169 to −146, and −134 to −119 in the coding (upper) strand and −219 to −193, −167 to −151, and −134 to −118 in the noncoding (lower) strand. It is also noticeable that these extracts induced DNase I-hypersensitive sites in the upper strand at nucleotide positions −139, −153, and −166 and in the lower strand at positions −160 and −176.

Figure 3:
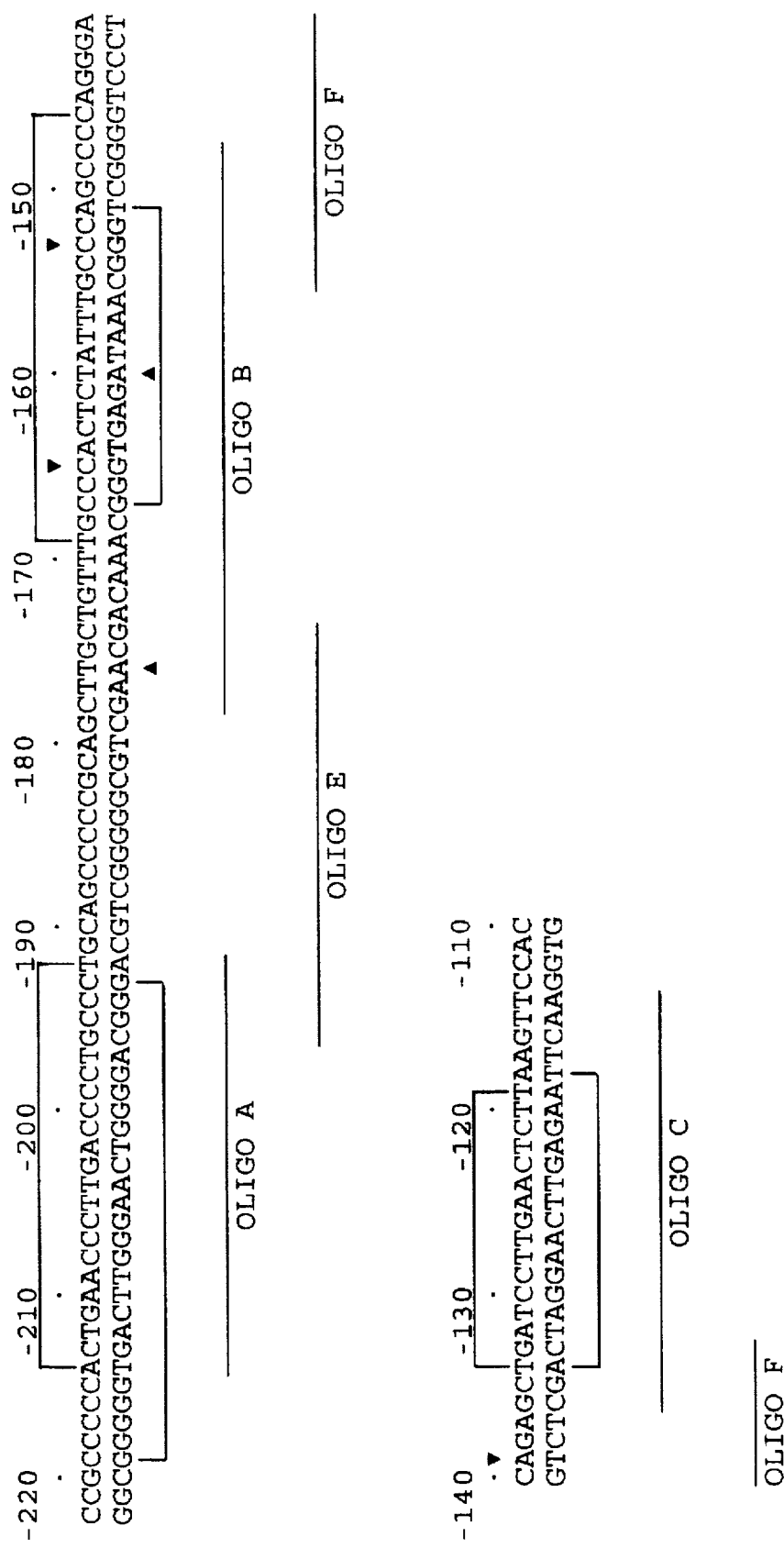
FIG. 3 shows the nucleotide sequence of the apoAI gene enhancer (region −222 to −110, SEQ ID NO:1) and summary of the DNase I protection patterns (bracketed) and DNase I-hypersensitive sites (∇).

Further confirmation of these results was obtained by using three double-stranded synthetic oligos corresponding to the −214 to −192 (oligo A), −178 to −148 (oligo B), −136 to −114 (oligo C) regions of the apoAI enhancer as probes for gel retardation assays with HepG2 cell nuclear extracts (FIG. 3). Each of these oligos formed retardation complexes that were inhibited by competition with the corresponding homologous oligos but not by two oligos corresponding to the −196 to −174 (oligo E) and −155 to −133 (oligo F) regions, which are located between the DNase I protection regions, or by λdIII or salmon sperm DNA. Interestingly, while the retardation complex formed with oligo B was not inhibited by competition with either oligo A or C, the complex formed with oligo A was inhibited by oligo C, and the complex formed with oligo C was competed for by oligo A. Cross-competition between oligos A and C was also observed in DNase I protection assays. Both DNase I protection regions corresponding to oligos A and C in the −256 to −80 DNA fragment were abolished by excess amounts of either oligo A or C, while only the protection region corresponding to oligo B was abolished by excess amounts of oligo B. As expected, excess amounts of either oligo E or F did not alter the DNase I protection pattern. Synergistic interactions between nuclear proteins mediate the transcriptional activity of the apoAI enhancer.

To determine whether nuclear protein binding mediates the transcriptional activity of the apoAI gene enhancer, nucleotides within each binding site were mutated (SEQ ID NO:2–7) so that protein binding is prevented. The activity of enhancer fragments with different combinations of these mutations was then determined by inserting them adjacent to the SV40 promoter in the vector pA10CATGEM4 and using the resulting constructs for CAT expression assays in HepG2 cells. The choice of nucleotides altered by mutagenesis (FIG. 4; SEQ ID NO: 2–7) was based on the observation that they are highly conserved in the corresponding nucleotide positions of the rat and chicken apoAI genes, and that double-stranded oligos similar to oligos A, B and C containing these mutations (oligos Amut, Bmut, and Cmut, respectively) do not form retardation complexes with HepG2 nuclear extracts and do not compete for binding of nuclear proteins with the corresponding apoAI enhancer sites in either gel retardation or DNase I protection assays. The results from the CAT expression assays showed that mutagenesis of any single site (SEQ ID NO: 2–4) reduced CAT activity to approximately one-third of that of the nonmutated enhancer, while mutagenesis of any two sites (SEQ ID NO: 5–7) resulted in CAT activity similar to that of the enhancerless vector pA10CATGEM4 (FIG. 4). Control experiments indicated that mutagenesis of nucleotides between these sites resulted in CAT activity not significantly different than that of the nonmutated enhancer. It is therefore clear, that binding of nuclear proteins to all three A, B, and C sites in the apoAI gene enhancer is essential for maximal transcriptional activity in HepG2 cells, and that binding of any of these proteins to a single site in the absence of binding of the others is not sufficient to generate transcriptional activity. Indeed, the CAT activities of constructs containing multiple copies of oligo A, B, or C, either proximal to the SV40 promoter in the vector pA10CATGEM4 or 41 nucleotides upstream from the transcription start site of the apoAI gene in the vector −41AI.CAT, were not significantly different from those of the vectors lacking these oligos in HepG2 cells.

These results suggest that the transcriptional activity of the apoAI gene enhancer is strongly dependent on synergistic interactions between nuclear proteins bound to Sites A, B, and C in HepG2 cells. In addition, these results indicate that binding of nuclear proteins to any two of these sites results in partial synergism, generating low levels of transcriptional activity, and that binding of nuclear protein (s) to the remaining third site further potentiates this synergism, leading to maximal levels of transcriptional activity.

Combination of different transcription factors determines the activity of the apoAI gene enhancer in hepatocytes.

Hepatocyte-specific expression of the apoAI gene was shown, as described below, to be determined by multiple transcription factors, some of which appear to be cell specific.

Recent studies with several liver-specific genes have led to the general concept that a common set of liver-specific transcriptional activators is responsible for coordinate expression of genes in hepatocytes. For example, binding of the transcription factor HNF-1 (also called LF-B1; Courtois et al., *Science*, 238:688–692 (1987)) to the regulatory regions of several liver-specific genes is essential and in certain cases, sufficient to drive liver-specific transcription. It is, therefore, interesting that a previously identified transcription factor called LF-A1, which is involved in activation of the α1-antitrypsin gene, binds to Site A in the apoAI gene enhancer (Hardon, E. M. et al., *EMBO J.*, 7:1711–1719 (1988)). Since LF-A1 is enriched in liver extracts, it is possible that it plays an important role in the hepatocyte-specific expression of the apoAI gene enhancer. However, several observations argue against this possibility. First, in contrast to Site A, the LF-A1 binding site of the α1-antitrypsin gene in conjunction with an Sp1-binding site is sufficient to stimulate liver-specific expression from heterologous promoters (Monaci, P. et al., *EMBO J.*, 7:2075–2087 (1988)). Second, gel retardation and DNase I protection assays indicate that in addition to LF-A1, Site A binds other nuclear proteins present in a wide variety of nonhepatic tissues; in fact, it binds several distinct members of a subfamily of the steroid/thyroid hormone receptor superfamily of transcription factors present in liver cells. Finally, the sequence 5'-TGAACCCTTGACCCCTG-3' (11–27 of SEQ ID NO: 1) present in Site A shows extensive similarity to the sequence 5'-TGAACCTTGCCTAGGG-3' (SEQ ID NO: 10) present in the binding site of HNF-4, a hepatocyte-enriched factor that plays a critical role in transthyretin gene expression (Costa, R. H. et al., *Mol. Cell. Biol.*, 9:1415–1425 (1989)). Indeed, in preliminary experiments, it has been determined that the recently cloned HNF-4 binds to Site A, and in cotransfection experiments, HNF-4 activates constructs containing one or multiple copies of Site A. Thus, the heterogeneity of proteins that bind to Site A suggests that this site may be an important target for modulation of expression of the apoAI gene by diverse signals. This interpretation, however, obscures the identity of the protein or proteins that, by binding to this site, contribute to the activation of the apoAI gene in liver cells.

The nucleotide sequence of Site C (89–104 of SEQ ID NO: 1) is very similar to that of Site A, (9–31 of SEQ ID NO: 1) and cross-competition experiments suggest that identical or very similar proteins in HepG2 cells bind to both of these sites. However, DNase I protection experiments indicate that, in contrast to Site A, which binds nuclear proteins present in both hepatic and nonhepatic cells, Site C binds proteins present only in hepatic cells. It is, therefore, not clear whether these sites bind the same or different proteins in HepG2 cells. It is noteworthy that in cotransfection experiments, increasing amounts of Site C, but not Site A, reduce the expression of apoAI gene constructs in HepG2 cells. This finding may suggest that in these cells the proteins that bind to Site C are different from those that bind to Site A.

It is possible that liver-specific expression of the apoAI gene is mediated, at least in part, by the protein(s) that binds to Site B. Indeed, nuclear extracts from nonhepatic tissues do not protect Site B from digestion by DNase I. Interestingly, as mentioned previously, Site B is composed of two tandem repeats –174-CTGTTTGCCCA-164 and –161-CT<u>A</u>T<u>T</u>TGCCCA-151, (49–59 and 62–72 of SEQ ID NO: 1) each of which differs respectively by only one or two nucleotides (underlined) from a sequence 5'-CTGATTGCCCA'-3' (SEQ ID NO: 11) present within an avid binding site for the transcription factor C/EBP, a liver-enriched factor involved in expression of several liver-specific genes.

It should also be noted that although there is limited sequence similarity between Sites B and C and the binding site for HNF-3, a family of hepatocyte-enriched factors involved in the expression of transthyretin, α1-antitrypsin, and α-fetoprotein genes, it is unlikely that the protein that binds to Site B or Site C is HNF-3. This argument is based on the observation that in contrast to Sites B and C, the HNF-3-binding site stimulates transcription in HepG2 cells (Costa, R. H. et al., *Mol. Cell. Biol.*, 9:1415–1425 (1989)). Clearly then, as with many other genes, hepatocyte-specific expression of the apoAI gene is determined not by a single cell-specific transcription factor but rather by multiple factors, some of which appear to be cell specific.

apoAI regulatory protein-1 (ARP-1)

To characterize the proteins that bind to Site A, an oligonucleotide that corresponded to the A site (oligo A) was used as a probe to screen several λgt11 cDNA expression libraries (Vinson et al., *Genes Dev.*, 2:801 (1988)). One positive clone (λHP-1) was isolated from a human placenta library and binding-specificity spot tests (Vinson et al. (1988)) showed that the fusion protein produced by λHP-1-infected bacteria bound specifically to oligo A. The sequence of the insert was determined (SEQ ID NO: 8) and its reading frame was established (FIGS. 5A–5B). The sequence of a clone that contained additional 5' sequences (λHP-16) revealed an upstream in-frame termination codon (underlined in FIGS. 5A–5B), thus, placing the initiator methionine at position 343/345 and predicting a 414 amino acid protein, (SEQ ID NO: 9) which is herein referred to as apoAI regulatory protein-1 (ARP-1).

Comparison of ARP-1 with proteins in the GenBank data base revealed similarity to human Ear-3 and Ear-2 "orphan" steroid hormone receptors (Miyajima et al., *Nucleic Acids Res.*, 16:11057 (1988)) and the Drosophila Seven-up proteins (types 1 and 2), which regulate retihal cell differentiation (Mlodzik et al., *Cell*, 60:211 (1990)). A cysteine-rich region of ARP-1 that corresponds to the DNA binding domain of the steroid hormone receptors (amino acids 79 to 144) (FIGS. 5A–5B), shares 98.5, 89.4 and 92.4% identity with the Ear-3, Ear-2 and Seven-up, respectively. The ARP-1 COOH-terminal domain (amino acids 145 to 414) is 95, 67 and 84.4% similar to Ear-3, Ear-2 and Seven-up (type 1), respectively, whereas the NH$_2$-terminal domain (amino acids 1 to 78) shows limited similarity. Thus, it appears that these proteins belong to an ancestral subfamily of nuclear receptors, which is referred to herein as the ARP subfamily. The high degree of evolutionary conservation of this subfamily suggests functional conservation and implies regulation of its members by similar ligands. The Ear-3 gene has been localized to human chromosome 5 (Miyajima et al. (1988)), whereas ARP-1 is on chromosome 15, indicating that these proteins are encoded by two distinct genes. Northern (RNA) blot analysis, with the use of an ARP-1 specific probe (3'-ARP gene probe; a ~2.2 kb genomic DNA fragment spanning 433 nucleotides at the 3' of λHP-1 and extending to 3' direction) revealed a single ~4.5 kb transcript in all human tissues (liver, intestine, placenta, kidney, spleen, lung, adrenal, thymus and heart) and cell types (HepG2, Hep3B, Caco-2, HeLa, HUSK-1 (skeletal myoblasts) and K562 (myelogenous leukemia)) examined. These results at least partially explain the ubiquitous tissue distribution of nuclear proteins that bind to Site A.

Translation in vitro of RNA derived from the insert of λHP-1 produced a protein of ~47 kD. Gel retardation analysis showed that in vitro translated ARP-1 bound specifically to oligo A, forming a complex similar in mobility to that of HeLa nuclear proteins. However, oligo C (a DNA probe that contains Site C) competed with formation of this complex. Methylation interference analysis demonstrated that the purine residues of oligo A that were contacted by in vitro translated ARP-1 were identical to those contacted by rat liver and HeLa nuclear proteins. Furthermore, ARP-1 produced in COS-1 cells protected Site A from DNase I cleavage. These results indicate that the DNA binding specificity of ARP-1 is identical to that of nuclear proteins that bind to Site A. Although ARP-1 bound to oligo C, it did not protect Site C from DNase I, suggesting that sequences surrounding this site may influence its interaction with ARP-1.

To determine whether ARP-1 can interact with cis-acting elements of other genes, in vitro-translated protein was tested for binding to several oligonucleotides. ARP-1 bound with high affinity and specificity to COUP (chicken ovalbumin), APOCIII (human apoCIII), APOB (human apoB), INS (rat insulin II) and TRE (thyroid-hormone responsive element), poorly to ERE (estrogen responsive element) and LF-B2, and not at all to HNF-4 (mouse transthyretin) and LF-A1. Binding to COUP and INS was not unexpected because the transcription factor that binds to these elements is Ear-3 (Wang et al., *Nature*, 340:163 (1989)), whose DNA binding domain is almost identical to that of ARP-1. In fact, Ear-3 also bound to elements recognized by ARP-1, which suggests that both proteins may be involved in the regulation of apoAI, apoCIII, apoB, insulin and ovalbumin genes.

The consensus sequence of the ARP-1 DNA binding sites is composed of two directly repeated octa-nucleotides and differs from various hormone responsive elements, which are generally palindromic repeats. However, ARP-1 also recognized the palindromic TRE. The property of ARP-1 to discriminate between TRE and ERE in combination with the ability of the thyroid hormone receptor to bind to both with opposite transcriptional effects may have significant implications for the regulation of genetic networks responsive to thyroid hormone.

Figure 6:
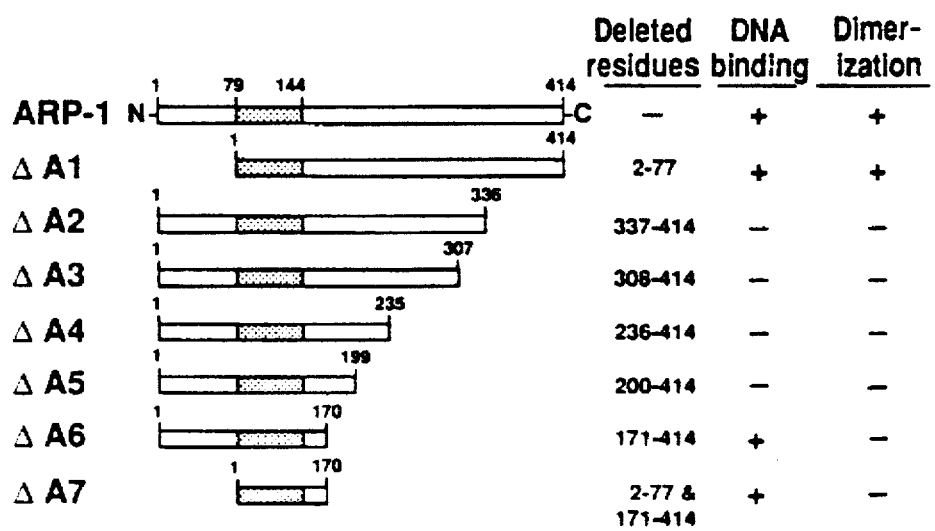
FIG. 6 is a schematic representation of the DNA binding and dimerization properties of ARP-1 and its deletion mutants. The DNA binding domain is shaded.

The DNA binding domain of ARP-1 was determined by testing several ARP-1 deletion mutants (FIG. 6) for binding to Site A. Deletion of amino acid residues 2 to 77 in mutant ΔA1 did not affect binding. In contrast, deletion of 78, 107, 179 or 215 residues at the COOH-terminal domain in mutants ΔA2, ΔA3, ΔA4 and ΔA5, respectively, eliminated binding; deletion of 244 residues in ΔA6 restored DNA binding. Moreover, deletion of both NH$_2$- and COOH-terminal domains in ΔA7 did not affect binding, thus mapping the DNA binding domain to between residues 78 and 170. These results indicate, that, in the absence of the 337–414 region, DNA binding is inhibited by sequences COOH to residue 170, and that at least a portion of these sequences is located in the 171 to 199 region.

To determine whether ARP-1 binds to DNA as a dimer, equal amounts of ARP-1 and ΔA1 mRNA were co-translated in vitro and the products were tested for binding to Site A in gel retardation assays. In addition to complexes that corresponded to ARP-1 and ΔA1 alone, complexes with intermediate mobility (heterodimers) were also formed, indicating that one molecule each of ARP-1 and ΔA1 bound concomitantly to Site A. Heterodimers were also formed when the two proteins were translated separately, mixed and used in gel retardation assays. These results indicate that ARP-1 binds to DNA as a dimer, the $NH_2$-terminal domain is not required for dimer formation, and dimerization can occur after translation. In contrast, heterodimers were not observed with any of the COOH-terminal deletion mutants, indicating that sequences within the COOH-terminal domain are required for formation of dimers that are capable of DNA binding, and that at least a portion of these sequences is located in the 337 to 414 region. Because mutants ΔA6 and ΔA7 lacked the COOH-terminal domain, they may have bound to DNA as monomers. Indeed, heterodimers were not observed when ΔA6 and ΔA7 were cotranslated. Thus, unlike the estrogen receptor, ARP-1 does not seem to contain a dimerization domain within its DNA binding region. The COOH-terminal domain of ARP-1 contains several hydrophobic heptad repeats, indicating its potential for coiled-coil interactions. Specifically, a heptad repeat in the region 357–391 is highly conserved among several steroid receptors and the analogous region of the estrogen receptor is required for dimerization and high-affinity DNA binding (Fawell et al., Cell, 60:953 (1990)).

Additional gel retardation experiments showed that over a wide range of concentrations, ARP-1 formed only one complex with oligo A. The curve of complex III formation has a sigmoidal shape, suggesting that ARP-1 binds to DNA cooperatively. In contrast, at low concentrations, ΔA6 formed one complex (complex I), but at high concentrations it formed an additional complex with reduced mobility (complex II). Thus, it seems that absence of the COOH-terminal domain in ΔA6 results in noncooperative binding of one (complex I) and subsequently two (complex II) molecules per binding site. Comparison of the protein amounts required to convert 50% of the probe into complex III (0.75 µg) and complex II (~50 µg), indicates that cooperative binding increases the DNA binding affinity by ~70 fold.

Taken together, these results suggest that sequences located COOH to residue 170 inhibit efficient DNA binding of ARP-1 monomers. The precise mechanism for this inhibition is not clear, but it is possible that the DNA binding domain is masked by a region in the COOH-terminal domain, either directly or by interacting with another protein as in the case of the glucocorticoid receptor and hsp90 (Godowski et al., Nature, 325: 365 (1987); Dalman et al., J. Biol. Chem., 264: 19815 (1989)). Dimerization of ARP-1, an event that requires the 337–414 region, results in presentation (unmasking) of the DNA binding domain and efficient binding to DNA.

Figure 7:
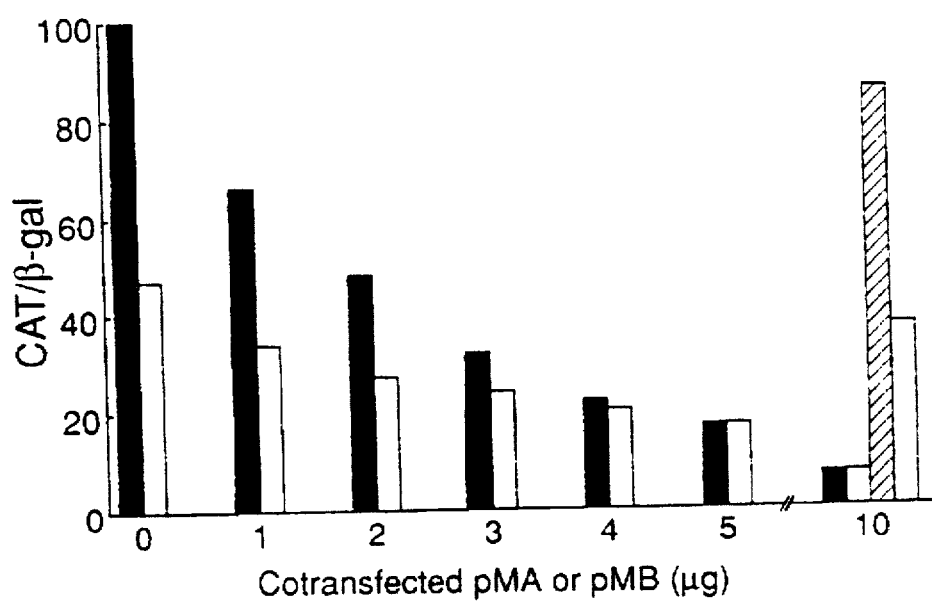
FIG. 7 is a diagrammatic representation of the repression of apoAI enhancer activity by ARP-1. The reporter plasmids −256AI.CAT (containing Sites A, B, and C) and −192AI.CAT (containing Sites B and C) (15 µg each), were cotransfected with pRSV-β-gal (3 µg) and the indicated amounts of pMA (ARP-1 gene in sense orientation) or pMB (ARP-1 gene in antisense orientation) in HepG2 cells. CAT assays were performed 48 hours after transfection, and the average values were normalized to β-galactosidase (β-gal) activities. Black bars, −256AI.CAT+pMA; white bars, −192AI.CAT+pMA; hatched bars, −256AI.CAT+pMB; stippled bars, −192AI.CAT+pMB.

To study the effect of ARP-1 on apoAI gene expression, reporter plasmids that contained the bacterial chloramphenicol acetyl transferase (CAT) gene under the control of the apoAI promoter and enhancer (–256AI.CAT and –192AI.CAT) were cotransfected (Sastry et al. (1988)) with increasing amounts of a construct expressing ARP-1 (pMA) into HepG2 cells (FIG. 7). Overexpression of ARP-1 repressed the expression of –256AI.CAT, containing Sites A, B, and C, but had a smaller effect on the activity of –192AI.CAT, containing Sites B and C, suggesting that the repression was mediated primarily through Site A, and to a lesser extent, through Sites B and C. However, ARP-1 did not affect the activity of a construct that contained one or multiple copies of Site A in front of the thymidine kinase promoter, suggesting that the ARP-1 does not function as a direct repressor, but that its effects on transcription may depend on promoter context.

Furthermore, preliminary experiments showed that both ARP-1 and Ear-3 downregulated the apoAI and apoCIII genes in HepG2 cells. The observation that high amounts of dietary fat and cholesterol significantly reduce hepatic apoAI mRNA (Miller et al., PNAS USA, 80:1511 (1983); Sorci-Thomas et al., J. Lipid Res., 30:1397 (1989)) raises the possibility that ARP-1 and Ear-3 may participate in mediating such effects. That ARP-1 and Ear-3 regulate apolipoprotein concentrations suggests that they may be an important part of the signal transduction mechanisms contributing to cholesterol homeostasis.

Retinoic acid response element in apoAI gene distinguishes between two different retinoic acid response pathways.

A retinoic acid response element (RARE) in the upstream regulatory region of the human apolipoprotein AI (apoAI) gene has been identified. Co-transfection studies showed a clearly preferential response of the apoAI gene element to the recently identified RXRα receptor, compared to the "classical" retinoic acid receptors RARα or RARβ. In contrast, the retinoic acid response element from the β laminin gene shows an opposite preference for RARα and RARβ over RXRα.

The role of RXRα in the regulation of cholesterol metabolism was further supported when the RXRα gene was cloned as a DNA binding protein of Site A. In a search for other factors capable of mediating positive transcriptional regulation via Site A, a human liver cDNA library was screened at low stringency using for a probe the sequence that codes for the DNA binding domain of ARP-1. One of the clones isolated using this procedure was subsequently determined to be identical with RXRα, a retinoic acid-responsive transcription factor (Mangelsdorf et al., Nature, 345:224–229 (1990)).

To determine whether Site A is the target site for RXRα, four repeats of this site (sequence −214 5'-ACTGAACCCTTGACCCCTGCCCT-3' −192; 9–31 of SEQ ID NO: 1) were introduced into a thymidine kinase-chloramphenicol acetyl transferase reporter (construct $A_4$-TK-CAT). This construct was transiently co-transfected in CV-1 cells with a eukaryotic expression vector for RXRα, in the presence or absence of retinoic acid ($10^{-6}$M). CV-1 cells were chosen because their levels of endogenous RARα and RXRα are below the threshold needed for ligand-dependent activation of the standard retinoic acid and thyroid hormone responsive element TREpal (Mangelsdorf et al. (1990); Sucov et al., Proc. Natl. Acad. Sci. USA, 87:539–546 (1990); Umesono et al., Nature, 336:262–265 (1988)). Exogenous expression of RXRα, in the presence of retinoic acid, resulted in a 300-fold increase above control levels of CAT activity (Table 2). Upregulation was dependent on the presence of both retinoic acid and RXRα. In contrast, a thymidine-kinase CAT reporter lacking Site A showed no change in activity with receptor co-transfection, with or without retinoic acid (data not shown). Co-transfection of $A_4$-TK-CAT with expression vectors for either RARα or RARβ, in the presence of retinoic acid, resulted in substantially less activation: 33-fold and 34-fold above control, respectively. In comparison, a duplicated insert of TREpal in TK-CAT (construct $M_2$-TK-CAT) was activated to roughly the same level (4–5 fold) by exogenous expression of RARα, RARβ or RXRαin the presence of retinoic acid. Thus, the preferential response to RXRα demonstrated by Site A was not due to a difference in the efficiency of receptor expression. When expressed in terms of the fold stimulation produced by the addition of retinoic acid to the test element and receptor, the same pattern of responsiveness was observed (see Table 2).

TABLE 2

Summary of Cotransfection Data

| Retinoic Acid Receptor | Retinoic Acid | Normalized CAT Activity | | | |
|---|---|---|---|---|---|
| | | M2-K-CAT | A4-TK-CAT | A1-TK-CAT | βLAM TK-CAT |
| None | − | 1.0 | 1.0 | 1.0 | 1.0 |
| | + | 0.9 | 0.8 | 0.7 | 1.0 |
| RARα | − | 0.7 | 0.6 | 0.5 | 8.8 |
| | + | 3.5 | 20 | 1.7 | 24 |
| RARβ | − | 0.7 | 1.0 | 0.6 | 6.3 |
| | + | 4.1 | 34 | 2.4 | 17 |
| RXRα | − | 0.9 | 1.6 | 0.6 | 1.2 |
| | + | 4.9 | 307 | 7 | 3.2 |

To demonstrate that a retinoic acid response element was not fortuitously created by the multimerization of Site A, single copies of Site A in both forward ($A_1$-TK-CAT) and reverse orientations were evaluated. RXRα, in the presence of retinoic acid, resulted in expression at seven times control levels for both orientations. In contrast, RARα and RARβ, in the presence of retinoic acid, resulted in expression at only twice control levels. When expressed as fold stimulation on the addition of retinoic acid, the pattern was the same: 12 fold for RXRα and 3–4 fold for RARα and RARβ. The TREpal can also function as a thyroid hormone responsive element (Glass et al., *Cell*, 54:313–325 (1988)). However, in a similar set of experiments, Site A reporter constructs (single and multimerized copies) did not respond to thyroid hormone receptor $α_1$ in the presence or absence of $T_3$ hormone (data not shown).

For comparison, the response of another retinoic acid response element to these two classes of retinoic acid receptors was assessed. A single copy of the β laminin RARE (Vasios et al., *Proc. Natl. Acad. Sci. USA*, 86:9099–9103 (1989)) was placed into the reporter TK-CAT (βLAM-TK-CAT). This β laminin reporter showed expression at 24 and 17 times control levels in response to RARα and RARβ, respectively, in the presence of retinoic acid. However, it exhibited only three times control activity with RXRα and retinoic acid. Thus, the pattern of responsiveness of the β laminin element appears to be opposite to that of Site A. However, RARα and RARβ, but not RXRα, produced a clear increase in expression of the β laminin construct in the absence of retinoic acid, minimizing the differences among the receptors when the data is expressed as fold stimulation upon addition of ligand.

In summary, of the three retinoic acid responsive elements evaluated, Site A showed a preferential response to RXRα, the β laminin retinoid response element showed a preferential response to RARα and RARβ, and the TREpal ($M_2$-TK-CAT) displayed a roughly equal responsiveness to all three retinoic acid receptors at the high concentration of retinoic acid used in these experiments.

Figure 8:
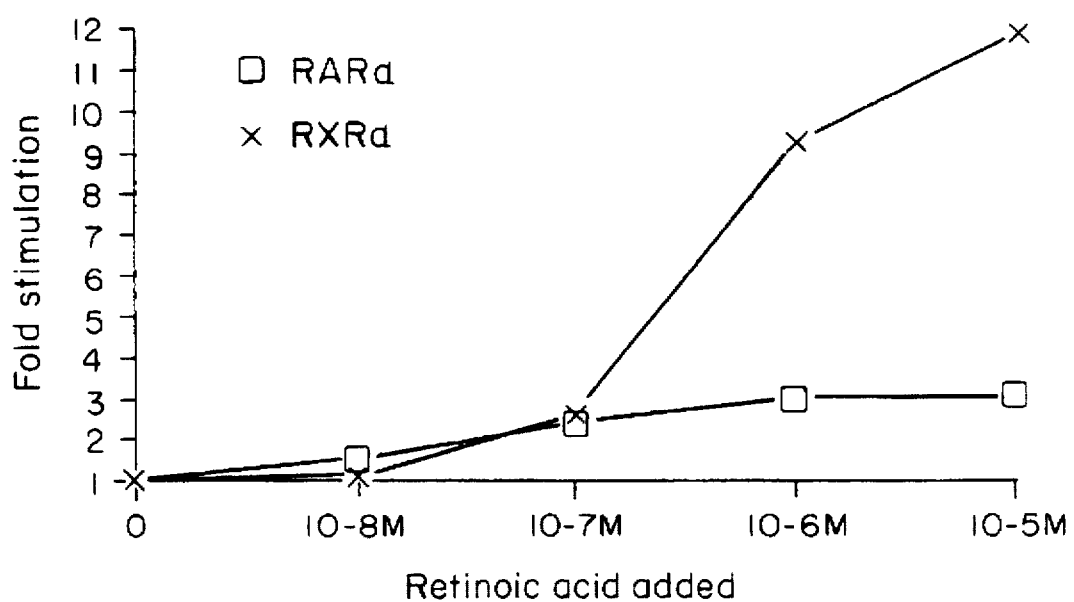
FIG. 8 shows the RARα and RXRα dose response to retinoic acid with A1-TK-CAT as the reporter. CV-1 cells were co-transfected with pMT2-RARα or pMT2-RXRα and A1-TK-CAT, and treated with increasing amounts of retinoic acid.

The dose-response relationship for RXRα and RARα activation of Site A revealed that RXRα required levels of retinoic acid exceeding $10^{-6}$M for maximal effect, while the RARα effect was nearly saturated at $10^{-7}$M (FIG. 8). This corresponds to the retinoic acid dose-response relationship previously described for the interaction of these receptors with the TREpal. Thus, at the levels of retinoic acid needed to produce a consistent effect of RXRα on the TREpal, a clearly preferential response of Site A to RXRα was consistently observed. The very high concentrations of retinoic acid required for this transcriptional effect suggest that the biological ligand for RXRα is a retinoid metabolite other than retinoic acid (Mangelsdorf et al. (1990)).

To evaluate whether the observed functional effects involved direct interaction of these receptors with the response elements, electrophoretic mobility shift assays were conducted using whole cell extracts from Cos cells transiently transfected with expression plasmids for RXRα or RARα. As a positive control, retardation complexes were formed between a single copy of the TREpal and either of these extracts. Binding was specific, since the retardation complexes were eliminated by 50-fold competition with unlabeled TREpal but not by 50-fold competition with an unrelated oligonucleotide. Extracts from Cos cells that were mock transfected produced no retardation complex. Formation of specific retardation complexes was observed with a single copy of Site A and either RARα- or RXRα- Cos cell extracts. It is noteworthy that Site A effectively cross-competed the interaction of both RARα and RXRα extracts with TREpal. This is not surprising, since Site A in single copy is functionally comparable to a duplicated copy of TREpal as a RARα responsive element, and is substantially more powerful as a RXRα responsive element. In contrast, the β laminin sequence, which effectively cross-competed binding of RARα extract from the TREpal, failed to compete for binding of RXRα to this same sequence. These binding data were consistent with the functional pattern, since the β laminin sequence is a powerful RARα responsive element but a poor RXRα responsive element.

Such binding studies suggest, but do not conclusively demonstrate, that the receptors bind directly to these responsive elements, since the complexes observed could involve proteins which are induced by the receptors. To address this possibility, RARα and RXRα prepared by in vitro translation were used in electrophoretic mobility shift assays. Reticulocyte lysates programmed with RARα or RXRα did not form specific complexes with either the TREpal or Site A. However, when these lysates were supplemented with untransfected Cos whole-cell extract, specific retardation complexes were formed. Unprogrammed reticulocyte lysate supplemented with untransfected Cos cell extract formed no retardation complex. Specific complex formation was abolished by pre-heating the Cos cell extracts to 65° C. These data suggest that the RARα and RXRα receptors themselves, rather than some secondarily induced products, are involved in the DNA-protein complexes, since addition of programmed reticulocyte lysate to untransfected Cos cell extract was necessary and sufficient for complex formation. The requirement for untransfected Cos cell extract indicates that other factors in the Cos cells, not induced by the receptors, are necessary for efficient binding. Such a requirement for auxiliary factors was also noted for other members of the steroid-thyroid receptor superfamily (Burnside et al., *J. Biol. Chem.*, 265:2500–2504 (1990); Murray and Towle, *Mol. Endo*, 3:1434–1442 (1989); Tsai et al., *Cell*, 50:701–709 (1987)).

Taken together, the functional and DNA-protein binding studies demonstrate that the apoAI Site A and β laminin retinoic acid responsive elements distinguish between two different retinoic acid responsive pathways: one in which signal transduction is mediated by RXRα, and another mediated by the "classical" retinoic acid receptors RARα and RARβ. Other transcriptional factors with intermediate affinities to the responsive elements may serve to further enforce and accentuate the distinction between these pathways, and permit them to subserve different cellular functions. When RXRα was identified, it was suggested that it may be involved in the regulation of vitamin A metabolism because of its tissue distribution (Mangelsdorf et al., *Nature*, 345:224–229 (1990)). The presence of an element with a preferential response to RXRα in the regulatory region of the apoAI gene, which is involved in the transport of lipids including vitamin A precursors, supports this hypothesis, and suggests that RXRα, or closely related receptors, may be central to these processes.

The identification of a retinoic acid responsive element in the regulatory region of the apoAI gene further suggests that expression of this gene may be responsive to retinoids. Indeed, preliminary results show that under appropriate conditions, expression of apoAI gene constructs in HepG2 cells can be upregulated by retinoic acid in the presence of co-transfected RXRα. Since apoAI Site A is also a target site for other members of the steroid/thyroid receptor superfamily, such as ARP-1, Ear-3/COUP and HNF-4, multiple regulatory signals, transduced by these factors, may converge at this site to affect expression of the apoAI gene. These observations suggest that retinoids, or other similar compounds, could play a role in regulating the apoAI gene, and thus, cellular cholesterol homeostasis.

Therapeutic, Diagnostic and Other Uses of the Present Invention

As a result of the work described herein, it is now possible to alter cholesterol and lipid metabolism, including vitamin A precursor metabolism, through several routes. For example, it has been shown that the apoAI gene includes three sites, each of which must be occupied by a protein for maximal activity of the apoAI enhancer and, thus, transcription of the gene. If maximal activity is desired, such as to increase production of apoAI and its availability for incorporation into HDL and chylomicrons, a protein(s) which binds an active site on the apoAI gene can be introduced into hepatic cells. Alternatively, a nucleic acid sequence (RNA or DNA) which encodes one or more proteins which bind an apoAI gene site can be introduced into cells in an appropriate vector, such as a retroviral vector, which expresses the encoded protein in the hepatic cells. The protein, or protein (s) bind one or more of the sites, resulting in maximal enhancer activity, and enhanced apoAI production.

As has been described herein, Site A has been shown to be responsive to both positive and negative regulatory proteins. Thus, it is possible, if desired, to enhance or reduce apoAI gene expression. As is also described herein, Site A of the apoAI gene has been shown to be a target for the RXRα receptor; that is, it has been shown to be a retinoic acid responsive element. For example, expression of apoAI gene constructs in liver cells can be upregulated by retinoic acid in the presence of co-transfected RXRα. As a result, it is reasonable to expect that expression of the apoAI gene in vivo is responsive to retinoids. Thus, retinoids or similar compounds can be administered in an amount sufficient to affect (upregulate) apoAI gene expression. The retinoid or other compound can be administered using known techniques; it can be administered, for example, orally, parenterally or intravenously.

It is also possible to identify the ligand for ARP-1 and alter lipid metabolism by administering the ligand or an analog of the ligand. For example, a drug which binds ARP-1 can be designed to mimic the activity of an ARP-1 ligand based on knowledge of the ligand structure, and administered to an individual to increase high density lipoprotein (HDL) synthesis and decrease low density lipoprotein (LDL) synthesis. As a result of the increased HDL levels, lipid transport to the liver and subsequent excretion is also enhanced. One example of a type of molecule which might be useful for this purpose is small lipophilic molecules which are in the class of terpenoids.

Using information provided herein, it is also possible to develop a diagnostic method by which an individual's ability to properly transport and excrete lipids can be assessed. For example, ARP-1 levels can be used as a diagnostic of apoAI expression; low ARP-1 levels would indicate high apoAI levels.

Also as a result of the work described herein, it is possible to screen existing compounds for their ability to alter apoAI gene expression and to design new compounds for that purpose. Existing compounds can be screened by assessing their ability to bind one or more of the three sites on the apoAI gene described herein. For example, existing compounds, including products present in microbial broths, can be screened for binding activity to Site A.

A further subject of the present invention is a hepatocyte-specific transcriptional enhancer and a method of hepatocyte-specific expression of a nucleic acid sequence of interest through the use of a construct containing the nucleic acid sequence of interest, the hepatocyte-specific transcriptional enhancer, and other components necessary for expression of the nucleic acid sequence of interest in hepatocytes. This can be used, for example, as a means of enhancing or replacing liver function in an individual whose liver function is compromised.

The invention will be further illustrated by the following exemplification, which is not intended to be limiting in any way.

EXEMPLIFICATION

Plasmid constructions

Essentially all plasmid constructs were made by the general procedures described previously (Sambrook, J. et al., *Molecular Cloning: A Laboratory Manual*, 2d Edition, Cold Spring Harbor Laboratory, Cold Spring Harbor, N.Y. (1989)). The structures of the resulting constructs were verified by restriction mapping and nucleotide sequencing.

The apoAI-chloramphenicol acetyltransferase (CAT) gene constructs –256AI.CAT, –192AI.CAT, –41AI.CAT and [SV]–41AI.CAT have been previously described (Sastry, K. N. et al., *Mol. Cell. Biol.*, 8:605–614 (1988)). Additional constructs were made by cloning several DNA fragments spanning different regions of the apoAI gene 5'-flanking sequences into a BamHI site engineered at the –41 nucleotide position in construct –41AI.CAT (Sastry, K. N. et al., *Mol. Cell. Biol.*, 8:605–614 (1988)). To generate fragments with ends compatible with the BamHI site, most of these fragments were first subcloned into the bacteriophage vector M13mp7 and then excised by using the flanking BamHI sites in the polylinker region of the vector. For the construction of –133AI.CAT, a HinfI-PstI fragment spanning the –366 to –41 region of the apoAI gene was subcloned in the PstI site of M13mp7. The fragment was subsequently excised by digestion of replicative-form DNA from this subclone with BamHI; after digestion at nucleotide position –133 with Sau3A, the –133 to –41 DNA fragment was cloned in the BamHI site of –41AI.CAT. Similarly, for the construction of –256[Δ–80/–41]AI.CAT, an MspI fragment spanning the –256 to –80 region was subcloned in the AccI site of M13mp7; after its excision by digestion of replicative-form DNA from this subclone with BamHI, the fragment was cloned in the BamHI site of –41AI.CAT. For the construction of −222[Δ−110/−41]ALCAT, a synthetic double-stranded oligonucleotide (oligo) spanning the −222 to −110 region of the apoAI gene with ends compatible with the BamHI restriction site was synthesized on a DNA synthesizer (Biosearch model 8600) and cloned into the BamHI site of −41ALCAT. For the construction of −203[Δ−133/−41]ALCAT, a Sau3A fragment spanning the −203 to −133 region of the rat apoAI gene (Haddad, I. A. et al., *J. Biol. Chem.*, 261:13268–13277 (1986)), the sequence of which is nearly identical to that of the corresponding region in the human apoAI gene, was cloned in the BamHI site of −41ALCAT. For the construction of −256[Δ−192/−41] ALCAT, a previously described apoALCAT gene fusion construct containing approximately 2.5 kb of the apoAI gene 5'-flanking sequences but lacking the −192 to −41 DNA region [construct Δ−192/−41ALCAT; Sastry et al. (1988)] was digested at the SmaI sites located at nucleotide position −256 and in the polylinker region 3' to the CAT gene, and the resulting fragment was cloned in pUC9.

The ability of various apoAI gene fragments to drive transcription from the heterologous SV40 early promoter was evaluated by using the SV40 early promoter-CAT gene fusion vector, pA10CATGEM4. pA10CATGEM4 was constructed by transferring a SalI-BamHI fragment, which contains the SV40 promoter and the CAT gene, from the previously described vector pA10CAT2 (Laimins, L. A. et al., *Proc. Natl. Acad. Sci. USA*, 79:6453–6457 (1982)) into pGEM4 (Promega Biotec, Madison, Wis.). pSV2CATGEM4, a vector similar to pA10CATGEM4 but containing the SV40 enhancer, was constructed by replacing a PvuII fragment that contains the SV40 early promoter and a part of the CAT gene in pA10CATGEM4 with the corresponding fragment from the previously described vector pSV2CAT (Gorman, C. M. et al., *Mol. Cell. Biol.*, 2:1044–1051 (1982)). Like pA10CAT2, the pA10CATGEM4 vector contains a BglII site proximal to the SV40 promoter and a BamHI site distal to this promoter (i.e., at the 3' end of the CAT gene). Several apoAI gene fragments with ends compatible with the BglII and BamHI sites were prepared as described above and cloned into pA10CATGEM4 in one or multiple copies (see FIG. 2).

Mutated versions of the −222 to −110 region in pA10CATGEM4 were constructed by using the oligo assembly method described previously (Karlsson, O. et al., *Proc. Natl. Acad. Sci. USA*, 84:8819–8823 (1987)). Seven synthetic oligos spanning the −222 to −110 region, some containing mutations (described below), were mixed in equimolar amounts, phosphorylated with T4 kinase (New England BioLabs, Inc., Beverly, Mass.), annealed by slow cooling from 65 to 25° C., and ligated into the BglII site of pA10CATGEM4.

Synthetic oligos

Oligos were synthesized on a Biosearch model 8600 DNA synthesizer, deblocked at 55° C., and purified through polyacrylamide gels as described previously (Sambrook, J. et al., *Molecular Cloning: A Laboratory Manual*, 2d Edition, Cold Spring Harbor Laboratory, Cold Spring Harbor, N.Y. (1989)). Complementary oligos spanning the −222 to −110, −214 to −192 (oligo A), −178 to −148 (oligo B), −136 to −114 (oligo C), −196 to −174 (oligo E), and −155 to −133 (oligo F) apoAI gene upstream region, all containing the tetranucleotide 5'-GATC-3' at their 5' ends, were synthesized, annealed, and used for cloning, for gel retardation and as competitors in DNase I protection assays described below. Mutated versions of oligos A, B and C (oligos Amut, Bmut and Cmut, respectively) were prepared similarly. The nucleotide substitutions in these oligos are indicated in FIG. 4 (see also SEQ ID NO: 2–7). The −222 to −110 apoAI gene region was also synthesized by annealing a mixture of three oligos spanning positions −221 to −183, −182 to −148 and −147 to −110 in the coding strand with four oligos spanning positions −221 to −193, −192 to −165, −164 to −129 and −128 to −110 in the noncoding strand. To facilitate cloning, −221 to −183 and −128 to −110 contained the tetranucleotide 5'-GATC-3' at their 5' ends. Mutated versions of the −222 to −110 DNA region were obtained by replacing appropriate oligos by their mutated version (see FIG. 4) in the annealing mixture.

Cell culture, transfections and CAT assays

Plasmid DNA from the various constructs was prepared and transfected into cultured cells by the calcium phosphate coprecipitation method as described previously (Sastry et al. (1988)). All cultured cells were maintained in Dulbecco's modified Eagle medium (GIBCO) supplemented with 10% fetal calf serum (Sigma Chemical Co., St. Louis, Mo.), penicillin and streptomycin at 37° C. in 5% $CO_2$. Human hepatoma (HepG2) cells were seeded at $4 \times 10^6$ cells per 100-mm dish, human colon carcinoma (Caco-2) cells were seeded at $2.5 \times 10^6$ cells per 100-mm dish, and other cell types (i.e., HeLa, NIH3T3 and C2) were seeded at $10^6$ cells per 100-mm dish, 1 day before transfection. To correct for variations in DNA uptake by the cells, 5 µg of plasmid pRSV-β-gal (Edlund, T. et al., *Science*, 230:912–916 (1985)) was cotransfected with each test construct. Protein extracts from transfected cells were made by three cycles of freeze-thaw as described previously (Sastry et al. (1988)). CAT (Gorman et al. (1988)) and β-galactosidase (β-gal) (Edlund et al. (1985)) enzyme activities in cell extracts were assayed as previously described, and for each experiment the CAT enzymatic activity was normalized to that of β-gal activity.

Nuclear extracts

HepG2 nuclear extracts were prepared from 10 confluent 150-mm dishes essentially as described previously (Dignam, J. D. et al., *Nucleic Acids Res.*, 11:1475–1489 (1983)) except that buffers A and C were supplemented with 1 mM phenylmethylsulfonyl fluoride (PMSF), and 1 µg each of pepstatin A and leupeptin (Sigma) per ml. Additionally, buffer C contained NaCl at a final concentration of 0.5M, and buffer D was replaced by a similar buffer, buffer G (20 mM N-2-hydroxyethylpiperazine-N'-2-ethane sulfonic acid [HEPES; pH 7.8], 0.1M KCl, 0.2 mM EDTA, 1 mM DTT, 1 mM PMSF, 20% glycerol). Aliquots of nuclear extracts were snap-frozen and stored in liquid nitrogen. The protein concentration of extracts was determined by the Lowry assay (Lowry, O. H. et al., *J. Biol. Chem.*, 193:265–275 (1951)) and was typically 3 to 8 mg/ml.

Gel retardation assays

Protein-DNA complexes were analyzed by electrophoresis in low-ionic-strength nondenaturing polyacrylamide gels as described previously (Fried, M. and D. M. Crothers, *Nucleic Acids Res.*, 9:6505–6525 (1981)). Approximately 15 µl of HepG2 cell nuclear extracts (10 µg of protein) in buffer G was mixed with poly(dI-dC) (2 µg; Pharmacia) in a final volume of 28 µl and incubated on ice for 10 min. Then 10 fmol of DNA fragments or synthetic oligos end labeled at their 5' ends with [γ$^{32}$P]ATP (New England Nuclear) and T4 polynucleotide kinase (New England BioLabs) in 2 µl of TE (10 mM Tris, 1 mM EDTA [pH 7.5]) was added, and incubation continued on ice for an additional 30 min. Subsequently 3 µl of buffer G supplemented with 60% (wt/vol) sucrose and 0.24% (wt/vol) bromophenol blue was added, and the mixture was loaded on a 4% polyacrylamide gel (80:1 acrylamide:bisacrylamide) made with 0.5x TBE buffer (1x TBE is 89 mM Tris base, 89 mM boric acid and 2 mM EDTA) and electrophoresed for 1.5 h at 200 V, using a Protein II gel apparatus (Bio-Rad Laboratories, Richmond, Calif.). Gels were fixed in 10% methanol-10% acetic acid, dried and exposed with X-ray film overnight at −70° C. with intensifying screens.

DNA binding specificity of ARP-1 assayed by gel retardation

The λHP-1 insert was subcloned in the Eco RI site of pGEM-4 (pGEM-ARP-1A), linearized with Xba I, transcribed in vitro by SP6 RNA polymerase, and the resulting RNA was translated in a rabbit reticulocyte lysate system (Promega) in the presence of [$^{35}$S]methionine. For gel retardation, proteins were incubated with $^{32}$P-labeled oligo A (10 fmol) for 30 min on ice in the presence of 10 mM Tris-HCl, pH 7.5, 50 mM NaCl, 5% glycerol, 1 mM EDTA, 1 mM DTT, and either 3 µg (for nuclear extracts) or 0.25 µg (for in vitro translated proteins) of poly (dI-dC), and separated by electrophoresis in non-denaturing gels. Complexes were competed with 50-fold molar excess of unlabeled oligo A, several double-stranded oligomers spanning the apoAI regions −136 to −114 (oligo C), −177 to −148, and −116 to −84, an unrelated oligomer, and oligo AMUT1.

DNase I protection assays

DNase I protection assays were carried out using a DNA fragment spanning the −256 to −80 region of the apoAI gene as a probe. The fragment was labeled with $^{32}$p at the 5' end of either the coding (upper) or noncoding (lower) strand as follows. For labeling of the upper strand, plasmid construct −256[Δ−80/−41]AI.CAT was digested at a HindIII site located in the polylinker region of the vector proximal to the −256 nucleotide position of the apoAI gene; after dephosphorylation with bacterial alkaline phosphatase (Bethesda Research Laboratories) and labeling with [γ$^{32}$P]ATP and T4 polynucleotide kinase, the plasmid was digested at a SalI site in the polylinker region of the vector proximal to the −80 nucleotide position of the apoAI gene. The resulting 176-bp radiolabeled fragment was subsequently isolated by polyacrylamide gel electrophoresis and electroelution onto DEAE filter strips (NA45; Schleicher & Schuell). Labeling of the lower strand was carried out exactly as described above except that digestion with SalI was done prior to labeling and digestion with HindIII was done after labeling. To a volume (usually 10 to 50 µl) of HepG2 nuclear extracts (75 to 120 µg of protein) in buffer G, 0.1 volume of 0.1 mM MgCl$_2$, 0.1 volume of 1 mg/ml poly(dI-dC), and 0.4 volume of 10% polyvinyl alcohol (Sigma) were added and the mixture was incubated on ice for 5 to 20 min. Then 0.4 volume of TE containing 1 to 2 fmol (approximately 10,000 cpm) of probe was added and incubation on ice continued for an additional 30 to 40 min. The mixture was subsequently incubated at 25° C. for 1 to 3 min; after addition of 0.1 volume of DNase I (25 µg/ml; Worthington) in 25 mM CACl$_2$-50 mM MgCl$_2$, incubation continued at 25° C. for 1 min. Then 5 volumes of stop solution (100 mM Tris hydrochloride [pH 8], 100 mM NaCl, 1% sodium dodecyl sulfate [SDS], 10 mM EDTA, 100 µg of proteinase K [Boehringer Mannheim, Indianapolis, Minn.] per ml, 25 µg of salmon sperm DNA [Sigma] per ml) was added; after incubation of the mixture at 65° C. for 15 min, the DNA was purified by phenol extraction and ethanol precipitation and analyzed on 7% polyacrylamide sequencing gels. Sequence coordinates were obtained by running in the same sequencing gel a G+A chemical sequencing ladder (Maxam, A. and W. Gilbert, Methods Enzymol., 65:499–560 (1980)), using the same end-labeled probe. DNase I digestion patterns in the absence of nuclear extracts were obtained as described above except that 1/10 as much DNase I was used.

Methylation interference analysis

The noncoding strand of oligo A was 5'-$^{32}$P-labeled, annealed with ~0.1-fold molar excess of its unlabeled complementary strand, partially methylated with dimethyl sulfate and used for preparative gel retardation. Protein-bound and free probe were recovered by electroelution onto NA-15 DEAE membrane (Schleicher & Schuell), incubated in 10 mM sodium phosphate-1 mM EDTA (pH 8.0) at 90° C. for 15 min, and then cleaved with 0.1M NaOH at 90° C. for 30 min. The samples (ARP-1, rat liver, and HeLa nuclear extracts) were precipitated with ethanol and analyzed on a 20% polyacrylamide-8M urea gel.

Transient co-transfections of test responsive elements with receptor expression vectors into CV-1 cells Test elements were inserted into TK-CAT (Kumar and Chambon, Cell, 55:145–156 (1988)) 105 bp upstream of the transcription start site of the HSV TK gene. cDNA coding sequences for RARα (Giguere et al., Mol. Cell. Biol., 10:2335–2340 (1990)), RARβ (Burnside et al., J. Biol. Chem., 256:2500–2504 (1990)) and RXRα were inserted in the PMT2 expression vector (Sambrook et al. (1989)). CV-1 cells were transiently transfected using calcium-phosphate co-precipitation with 10 µg reporter and 5 µg receptor expression vector (200 µg receptor expression vector produced similar results). MLV β gal was used as a control for transfection efficiency. Cells were grown in DME with 10% newborn calf-serum stripped with anion exchange resin and activated charcoal. DMSO alone, or DMSO with retinoic acid, was added to 10$^{-6}$M, 10$^{-8}$M, 10$^{-5}$M or 10$^{-7}$M retinoic acid. CAT and β gal activity were assayed (Sambrook et al. (1989)), and CAT activity was corrected for transfection efficiency. Control represents co-transfection with anti-sense RXRα in PMT2, but the same CAT activity was seen on co-transfection with anti-sense RARα and with an unrelated sequence in PMT2. Corrected activity is expressed as fold activation over control.

DNA-protein complex formation between response elements and RXRα and RARα

Cos cells were transiently transfected with retinoic acid receptor PMT2 expression vectors for RARα or RXRα, and harvested for whole cell extracts 48 hours later (Kumar and Chambon, Cell, 55:145–156 (1988)). 5 µg of cell extract was pre-incubated for 10 min on ice in the presence of 10 mM Tris-HCl pH 7.5, 50 mM NaCl, 5% glycerol, 1 mM EDTA, 1 mM DTT and 2 µg poly(dI-dC) 50 fmol of double-stranded oligonucleotide probe end-labeled with [γ-$^{32}$P] ATP and a 50-fold molar excess of competitor (apoAI Site A, β laminin, TREpal) were added together as indicated and incubated at room temperature for 15 minutes (final volume 20 µl). Complexes were then resolved by electrophoresis through 6% polyacrylamide. The fraction of total counts in the specific retarded complex were averaged on repeated independent experiments for quantification.

EQUIVALENTS

Those skilled in the art will recognize, or be able to ascertain using no more than routine experimentation, many equivalents to the specific embodiments of the invention described herein. Such equivalents are intended to be encompassed by the following claims:

We claim:

1. A method of screening for a compound which alters apolipoprotein AI gene expression comprising the steps of:
   a) contacting a culture of hepatocytes with the compound, said hepatocytes comprising a transcriptional enhancer of the apolipoprotein AI gene, operably linked to a promoter and a gene under control of said promoter, thereby generating a test culture;
   b) incubating the test culture under conditions appropriate for expression of said gene; and
   c) assessing expression of said gene, wherein a change in expression of said gene is indicative of the ability of the compound to alter expression of the apolipoprotein AI gene.

2. The method of claim 1, wherein the transcriptional enhancer is depicted in SEQ ID NO:1.

3. The method of claim 1, wherein said gene is a reporter gene.

4. The method of claim 1, wherein said gene is an apolipoprotein AI gene.

5. The method of claim 1, wherein the compound is present in microbial broths.

6. The method of claim 1, wherein the transcriptional enhancer, the promoter and the gene under control of said promoter are contained in a plasmid construct.

7. The method of claim 1, wherein the compound is a gene product of DNA transfected into the hepatocytes.

8. The method of claim 3, wherein the reporter gene is a bacterial chloramphenicol acetyl transferase (CAT) gene.

9. A method of screening for a compound which alters apolipoprotein AI gene expression comprising the steps of:
   a) incubating the compound with a hepatocyte nuclear extract and a transcriptional enhancer of the apolipoprotein AI gene or a DNA sequence of at least one site in the transcriptional enhancer, the site selected from the group consisting of Site A, Site B, Site C and combinations thereof, under conditions appropriate for formation of a complex comprising the transcriptional enhancer and the nuclear extract;
   b) assessing complex formation obtained in step a); and
   c) comparing complex formation assessed in step b) with formation of a complex comprising the transcriptional enhancer and the nuclear extract of step a) in the absence of the compound, wherein a difference in complex formation in the presence of the compound and complex formation in the absence of the compound is indicative of the ability of the compound to alter apolipoprotein AI gene expression.

10. The method of claim 9, wherein the transcriptional enhancer is depicted in SEQ ID NO:1.

11. The method of claim 9, wherein the DNA sequence is of one site in the transcriptional enhancer.

12. The method of claim 9, wherein the compound is present in microbial broths.

13. A method of screening for a compound which alters apolipoprotein AI gene expression comprising the steps of:
   a) incubating a transcriptional enhancer of the apolipoprotein AI gene with the compound and a composition comprising a binding protein that binds to a DNA sequence of at least one site in the transcriptional enhancer, the site selected from the group consisting of Site A, Site B, Site C and combinations thereof, under conditions appropriate for formation of a complex comprising the transcriptional enhancer and the binding protein;
   b) assessing complex formation obtained in step a); and
   c) Comparing complex formation assessed in step b) with formation of a complex comprising the transcriptional enhancer and the binding protein of step a) in the absence of the compound, wherein a difference in complex formation in the presence of the compound and complex formation in the absence of the compound is indicative of the ability of the compound to alter apolipoprotein AI gene expression.

14. The method of claim 13, wherein the transcriptional enhancer and the binding protein are incubated together under conditions appropriate for formation of a complex comprising the transcriptional enhancer and the binding protein prior to addition of the compound.

15. The method of claim 13, wherein the transcriptional enhancer is depicted in SEQ ID NO:1.

16. The method of claim 13, wherein the binding protein is selected from the group consisting of:
   a) ARP-1;
   b) a heterodimer consisting essentially of ARP-1 and RXRα; and
   c) Ear-3.

17. The method of claim 13, wherein the compound is present in microbial broths.

18. The method of claim 16, wherein the binding protein has the amino acid sequence depicted in SEQ ID NO:9.

* * * * *